United States Patent
Zheng

(10) Patent No.: US 10,590,472 B2
(45) Date of Patent: Mar. 17, 2020

(54) METHODS OF DETECTING NUCLEIC ACIDS AND APPLICATIONS THEREOF

(71) Applicant: Zhi Zheng, Fullerton, CA (US)

(72) Inventor: Zhi Zheng, Fullerton, CA (US)

(*) Notice: Subject to any disclaimer, the term of this patent is extended or adjusted under 35 U.S.C. 154(b) by 98 days.

(21) Appl. No.: 15/508,861

(22) PCT Filed: Sep. 4, 2015

(86) PCT No.: PCT/US2015/048703
§ 371 (c)(1),
(2) Date: Mar. 3, 2017

(87) PCT Pub. No.: WO2016/037142
PCT Pub. Date: Mar. 10, 2016

(65) Prior Publication Data
US 2017/0275684 A1 Sep. 28, 2017

Related U.S. Application Data

(60) Provisional application No. 62/046,810, filed on Sep. 5, 2014.

(51) Int. Cl.
*C12P 19/34* (2006.01)
*C12Q 1/6853* (2018.01)
*C12Q 1/6834* (2018.01)

(52) U.S. Cl.
CPC ......... *C12Q 1/6853* (2013.01); *C12Q 1/6834* (2013.01)

(58) Field of Classification Search
CPC ............ C12Q 1/6853; C12Q 2565/519; C12Q 1/6834
USPC ...................................................... 435/91.2
See application file for complete search history.

(56) References Cited

U.S. PATENT DOCUMENTS

| | | | |
|---|---|---|---|
| 6,020,138 A | 2/2000 | Akhavan-Tafti | |
| 2005/0037346 A1 | 2/2005 | Barany et al. | |
| 2006/0105337 A1 | 5/2006 | Warner et al. | |
| 2006/0263769 A1* | 11/2006 | Luo | C12Q 1/6834 435/5 |
| 2006/0286583 A1* | 12/2006 | Luo | C12Q 1/682 435/6.12 |
| 2012/0034603 A1* | 2/2012 | Oliphant | C12Q 1/6827 435/6.11 |
| 2014/0066318 A1* | 3/2014 | Frisen | C12Q 1/6841 506/3 |

FOREIGN PATENT DOCUMENTS

| EP | 1311703 B1 | 5/2008 |
|---|---|---|
| WO | WO-2003/064692 A1 | 8/2003 |

OTHER PUBLICATIONS

Voelkerding, K.V. et al. (Apr. 2009, e-published on Feb. 26, 2009). "Next-generation Sequencing: From Basic Research to Diagnostics," *Clinical Chemistry* 55(4):641-658.

International Search Report dated Jan. 26, 2016 for International Application No. PCT/US2015/048703, filed on Sep. 4, 2015, four pages.
Arefian, E. et al. (Jul. 1, 2011; e-pub. Apr. 12, 2011). "Analysis of microRNA Signatures Using Size-Coded Ligation-Mediated PCR," *Nucleic Acids Res.* 39(12):e80, pp. 1-7.
Bustin, S.A. et al. (Sep. 2004). "Pitfalls of Quantitative Real-Time Reverse-Transcription Polymerase Chain Reaction," *J. Biomol. Tech.* 15(3):155-166.
Cheng, Z. et al. (Jan. 2013, e-pub. Oct. 24, 2012). "A Novel, Sensitive Assay for High-Throughput Molecular Detection of Plasmodia for Active Screening of Malaria for Elimination," *J. Clin. Microbiol.* 51(1):125-130.
Cotter, C. et al. (Sep. 7, 2013, e-pub. Apr. 15, 2013). "The Changing Epidemiology of Malaria Elimination: New Strategies for New Challenges," *Lancet* 382(9895): 900-911.
Dimitrov, R.A. et al. (Jul. 2004). "Prediction of Hybridization and Melting for Double-Stranded Nucleic Acids," *Biophys. J.* 87(1):215-226.
Holmberg, A. et al. (Mar. 2005). "The Biotin-Streptavidin Interaction can be Reversibly Broken Using Water at Elevated Temperatures," *Electrophoresis* 26(3):501-510.
Hopkins, H. et al. (Aug. 15, 2013). "Highly Sensitive Detection of Malaria Parasitemia in a Malaria-Endemic Betting: Performance of a New Loop-Mediated Isothermal Amplification Kit in a Remote Clinic in Uganda," *J. Infect. Dis.* 208(4):645-652.
Hsuih, T.C.H. et al. (Mar. 1996). "Novel, Ligation-Dependent PCR Assay for Detection of Hepatitis C in Serum," *J. Clin. Microbiol.* 34(3):501-507.
International Preliminary Report on Patentability dated Mar. 16, 2017 for International Application No. PCT/US2015/048703, filed on Sep. 4, 2015, seven pages.
Lun, F.M. et al. (Dec. 16, 2008; E-pub. Dec. 5, 2008). "Noninvasive Prenatal Diagnosis of Monogenic Diseases by Digital Size Selection and Relative Mutation Dosage on DNA in Maternal Plasma," *Proc. Natl. Acad. Sci. USA* 105(50):19920-19925.
Mens, P.F. et al. (2006; e-pub. Oct. 3, 2006). "Detection and Identification of Human Plasmodium Species With Real-Time Quantitative Nucleic Acid Sequence-Based Amplification," *Malar. J.* 5:80, 6 pages.
Mitra, S.A. et al. (Feb. 15, 2012; e-pub. Dec. 14, 2011). "A Central Role for Long Non-Coding RNA in Cancer," *Front. Genet.* 3(Article 17):1-9.
Miura, N. et al. (2008). "Serum Messenger RNA as a Biomarker and its Clinical Usefulness in Malignancies," *Clin. Med. Oncol.* 2:511-527.

(Continued)

*Primary Examiner* — Cynthia B Wilder
(74) *Attorney, Agent, or Firm* — Morrison & Foerster LLP

(57) ABSTRACT

The present application provides simple, specific and sensitive methods for detecting a target nucleic acid in a biological sample, detecting a pathogen in a biological sample, and diagnosing a disease in an individual, utilizing a combination of nucleic acid hybridization-based capture and ligation-enabled PCR. The methods are particularly useful for detecting low level nucleic acids and pathogens and for automation and processing of multiple biological samples.

18 Claims, 10 Drawing Sheets

Specification includes a Sequence Listing.

(56) References Cited

OTHER PUBLICATIONS

Murphy, S.C. et al. (Mar. 1, 2012). "Real-Time Quantitative Reverse Transcription PCR for Monitoring of Blood-Stage Plasmodium Falciparum Infections in Malaria Human Challenge Trials," Amer. J. Trop. Med. Hyg. 86 (3):383-394.

Ng, E.K. et al. (Aug. 2002). "Presence of Filterable and Nonfilterable mRNA in the Plasma of Cancer Patients and Healthy Individuals," Clin. Chem. 48(8):1212-1217.

Okell, L.C. et al. (Dec. 4, 2012). "Factors determining the occurrence of submicroscopic malaria infections and their relevance for control," Nature Communications 3:1237, pp. 1-9.

Rougemont, M. et al. (Dec. 2004). "Detection of Four Plasmodium Species in Blood From Humans by 18S-RNA Gene Subunit-Based and Species-Specific Real-Time PCR Assays," J. Clin. Microbiol. 42(12):5636-5643.

Saiki, R.K. et al. (Jan. 29, 1988). "Primer-Directed Enzymatic Amplification of DNA With a Thermostable DNA Polymerase," Science 239(4839):487-491.

Schneider, P. et al. (Jan. 2005). "Real-Time Nucleic Acid Sequence-Based Amplification is More Convenient Than Real-Time PCR for Quantification of Plasmodium Falciparum," J. Clin. Microbiol. 43(1):402-405.

Skog, J. et al. (Dec. 2008; e-pub. Nov. 16, 2008). "Glioblastoma Microvesicles Transport RNA and Proteins that Promote Tumour Growth and Provide Diagnostic Biomarkers," Nat. Cell Biol. 10(12):1470-1476, 16 pages.

Sokolova, N.I. et al. (May 1988). "Chemical Reactions within DNA Duplexes," FEBS Letters 232(1):153-155.

Xu, Y. et al. (Feb. 1, 2001). "Nonenzymatic Autoligation in Direct Three-Color Detection of RNA and DNA Point Mutations," Nat. Biotech. 19(2):148-152.

Zheng, Z. et al. (Jul. 2006). "Sensitive and Quantitative Measurement of Gene Expression Directly from a Small Amount of Whole Blood," Clin. Chem. 52(7):1294-1302.

* cited by examiner

SEQUENCE LISTING

<160> NUMBER OF SEQ ID NOS: 8

<210> SEQ ID NO 1
<211> LENGTH: 49
<212> TYPE: DNA
<213> ORGANISM: Artificial Sequence
<220> FEATURE:
<223> OTHER INFORMATION: Synthetic Construct

<400> SEQUENCE: 1
tggaagtatt ttagacaaat gctttctttt tggtcatagc tgtttcctg    49

<210> SEQ ID NO 2
<211> LENGTH: 47
<212> TYPE: DNA
<213> ORGANISM: Artificial Sequence
<220> FEATURE:
<223> OTHER INFORMATION: Synthetic Construct

<400> SEQUENCE: 2
tgtaaaacga cggccagttt tttcgacggt atctgatcgt cttcact    47

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
cccttaactt tcgttcttga ttaa    24

<210> SEQ ID NO 4
<211> LENGTH: 26
<212> TYPE: DNA
<213> ORGANISM: Artificial Sequence
<220> FEATURE:
<223> OTHER INFORMATION: Synthetic Construct

<400> SEQUENCE: 4
tctaagaatt tcacctctga catctg    26

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct

<400> SEQUENCE: 5
gcagttgttc gtctccagaa aa    22

<210> SEQ ID NO 6
<211> LENGTH: 25
<212> TYPE: DNA
<213> ORGANISM: Artificial Sequence
<220> FEATURE:
<223> OTHER INFORMATION: Synthetic Construct

<400> SEQUENCE: 6
tcggcatagt ttatggttaa gatta    25

<210> SEQ ID NO 7
<211> LENGTH: 18
<212> TYPE: DNA
<213> ORGANISM: Artificial Sequence

```
<220> FEATURE:
<223> OTHER INFORMATION: Synthetic Construct

<400> SEQUENCE: 7
tgtaaaacga cggccagt                                                   18

<210> SEQ ID NO 8
<211> LENGTH: 18
<212> TYPE: DNA
<213> ORGANISM: Artificial Sequence
<220> FEATURE:
<223> OTHER INFORMATION: Synthetic Construct

<400> SEQUENCE: 8
caggaaacag ctatgacc                                                   18
```

METHODS OF DETECTING NUCLEIC ACIDS AND APPLICATIONS THEREOF

CROSS-REFERENCE TO RELATED APPLICATIONS

This application is a National Phase Application under 35 U.S.C. 517 371 of International Application No. PCT/US2015/048703, filed Sep. 4, 2015, which claims priority to U.S. Provisional Patent Application No. 62/046,810, filed on Sep. 5, 2014, and titled "Methods of detecting nucleic acids and applications thereof," which are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 739542000100SEQLIST.txt, date recorded: Jan. 25, 2017, size: 2 KB).

BACKGROUND OF INVENTION

Nucleic acids, as diagnostic targets, are of great importance in clinical settings. For many years, DNA has been successfully used as a molecular target for the diagnosis of many diseases, including prenatal conditions (Lun et al., Proc. Natl. Acad. Sci. USA 105(50): 19920-5, 2008), cancer (Gormally et al., Mutat. Res. 635(2-3): 105-17, 2007) and infectious diseases (Hawkes and Kain, Expert Rev. Anti Infect. Ther. 5(3): 485-95, 2007). DNA-based diagnostics include polymerase chain reaction (PCR) (Rougemont et al., J. Clin. Microbiol. 42(12): 5636-43, 2004), loop-mediated isothermal amplification (LAMP) (Hopkins et al., J. Infect. Dis. 208(4); 645-652, 2013), etc., which all offer sensitive detection of target DNA. However, they largely rely on extraction of DNA before detection, and the extraction process can be laborious and prone to contamination. This is particularly problematic in settings where large numbers of samples are being processed.

RNA is also a good target for diagnostics (Miura et al., Clin. Med. Oncol. 2: 511-27, 2008; Ng et al., Clin. Chem. 48(8): 1212-7, 2002; Skog et al., Nat. Cell Biol. 10(12): 1470-U209, 2008; Murphy et al., Amer. J. Trop. Med. Hyg. 86(3): 383-94, 2012; Mens et al., Malar. J. 5: 80, 2006; Mitra et al., Front. Genet. 3: 17, 2012). Current RNA detection methods primarily include microarray hybridization, reverse transcription PCR, nucleic acid sequence-based amplification (NASBA) and RNA hybridization assays. Microarray assays are capable of measuring the expression levels of large numbers of genes simultaneously or genotyping multiple regions of a genome in a single RNA sample. Yet when only a small number of genes are required to be tested in a large number of samples, as in clinical diagnostic settings, the use of microarrays becomes impractical, as the cost-effectiveness is low and labor demand is high. Reverse transcription PCR is currently the most widely used technique for RNA quantification, but as it depends on purification and reverse transcription of RNA, the accuracy and reproducibility of quantification can be reduced by varied efficiencies of extraction and reverse transcription processes (Bustin and Nolan, J. Biomol. Tech. 15(3): 155-66, 2004). NASBA (Schneider et al., J. Clin. Microbiol. 43(1): 402-5, 2005) and size-coded ligation-mediated polymerase chain reaction (SL-PCR) (Arefian et al., Nucleic Acids Res. 39(12), 2011) detect RNA without prior reverse transcription, enabling specific, sensitive, quantitative detection of RNA. However, they both still rely on extraction of RNA and decontamination of DNA, which are expertise-demanding and error-prone processes (Peirson and Butler, Methods Mol. Biol. 362: 315-27, 2007).

A hybridization-based RNA detection technique, previously developed by the inventor, avoided RNA purification and reverse transcription, measuring RNA levels sensitively and specifically in whole blood with high throughput (Zheng et al., Clin. Chem. 52(7): 1294-302, 2006). Although capable of multiplex detection, this method requires specially-made, branched DNA multimers as signal amplifiers, which hinders its application in ordinary laboratory settings.

Ligation-dependent PCR assay (Hsuih et al., J. Clin. Microbiol. 34(3): 501-7, 1996) also detects RNA without the need for RNA extraction or reverse transcription. The assay uses two DNA capture probes for RNA isolation and two DNA hemiprobes for subsequent PCR. The DNA capture probes have a target-complementary sequence as well as a biotin moiety, which can bind to a surface with streptavidin. The two DNA hemiprobes are designed to bind to target RNA in juxtaposition to one another. Target RNA is directly purified from sample lysate by capture probes anchored to a solid surface through the interaction between biotin and streptavidin. The hemiprobes can then be linked to each other by incubation with a ligase (see EP1311703) to form a full probe that serves as a template for PCR.

All references discussed herein are incorporated by reference in their entirety.

BRIEF SUMMARY OF THE INVENTION

In one aspect, the invention provides a method of detecting a target nucleic acid in a biological sample, comprising: a) capturing said target nucleic acid through a plurality of capture extenders, wherein each of the capture extenders comprises a capturing sequence that hybridizes to a region on the target nucleic acid (such region on the target nucleic acid referred to herein as a capture targeting sequence) and an immobilizing sequence that hybridizes to a capture probe conjugated to a solid support, thereby immobilizing the target nucleic acid to the solid support; b) contacting the target nucleic acid with a plurality of detection probes, wherein each of the plurality of detection probes comprises a sequence that hybridizes to a region on the target nucleic acid (such region on the target nucleic acid referred to herein as a detection targeting sequence); c) ligating said plurality of detection probes to form a ligated detection sequence, wherein the detection probes are hybridized to the target nucleic acid immobilized to the solid support; d) amplifying said ligated detection sequence; and e) detecting the amplified ligated detection sequence.

In some embodiments, the plurality of detection probes comprises a 5' detection probe and a 3' detection probe, wherein the region of the target nucleic acid that is complementary to a sequence in the 5' detection probe (said region of the target nucleic acid being the 5' detection probe's detection targeting sequence) is 5' to the region of the target nucleic acid that is complementary to a sequence in the 3' detection probe (said region of the target nucleic acid being the 3' detection probe's detection targeting sequence). In yet another embodiment, the plurality of detection probes further comprises at least one internal detection probe that is complementary to a region of the target nucleic acid between the detection targeting sequences of the 5' and 3' detection probes. In some embodiments, the 5' detection probe and any internal detection probes are phosphorylated at their 5' ends. In some embodiments, the 5' detection probe and any internal detection probes are not phosphorylated at their 5' ends.

In some embodiments, the ligating step is carried out by a ligase, such as T4 ligase. In some embodiments, the ligating step is carried out by a ligase, such as T4 ligase, after any gaps between the detection probes when hybridized to the target nucleic acid have been filled in with a polymerase or reverse transcriptase. In some embodiments, the detection probes are unphosphorylated, and the ligating step is carried out by a ligase, such as T4 ligase, after phosphorylating the detection probes with a polynucleotide kinase, such as T4 polynucleotide kinase.

In some embodiments, the amplification step comprises PCR amplification using a first primer complementary to a region on the 5' detection probe and a second primer corresponding to a region on the 3' detection probe.

In some embodiments, the target nucleic acid is within a cell. In some embodiments, the target nucleic acid is not within a cell. In some embodiments, the target nucleic acid is RNA. In some embodiments, the RNA is mRNA, ribosomal RNA, a splice isoform of an mRNA, or non-coding RNA. In some embodiments, the ribosomal RNA is 18S ribosomal RNA.

In yet another embodiment, the target nucleic acid is DNA.

In some embodiments the biological sample is selected from the group consisting of a cell lysate, a tissue homogenate, a blood sample, a dried blood spot, a plasma sample, a serum sample, a blood clot, a nasal swab, a pharyngeal swab, a cheek swab, urine, and saliva.

In some embodiments, the method is high-throughput.

In another aspect, the invention provides a method of diagnosing a disease in an individual. In some embodiments, the disease is caused by a pathogen. In some embodiments, the disease, such as an infectious disease, is diagnosed by detecting a nucleic acid of the pathogen in a biological sample derived from the individual. In some embodiments, the disease is associated with an abnormal target nucleic acid (such as circulating tumor nucleic acid or prenatal nucleic acid in a body fluid sample), and is diagnosed by detecting the abnormal target nucleic acid in a biological sample derived from the individual.

In yet another aspect, the invention provides a method of detecting a genetic variation (such as a mutation) in an individual. In some embodiments, the genetic variation is associated with a disease.

In yet another aspect, the invention provides a method of detecting a foreign nucleic acid in a biological sample. In some embodiments, the source of the foreign nucleic acid is selected from the group consisting of a contaminant, a pathogen, etc.

In some embodiments, there is provided a method for detecting a plurality of target nucleic acids in a biological sample.

In some embodiments, there is provided a method for screening a large number of samples for the presence of one or more target nucleic acids using a matrix pooling strategy.

DETAILED DESCRIPTION OF THE INVENTION

Figure 1:
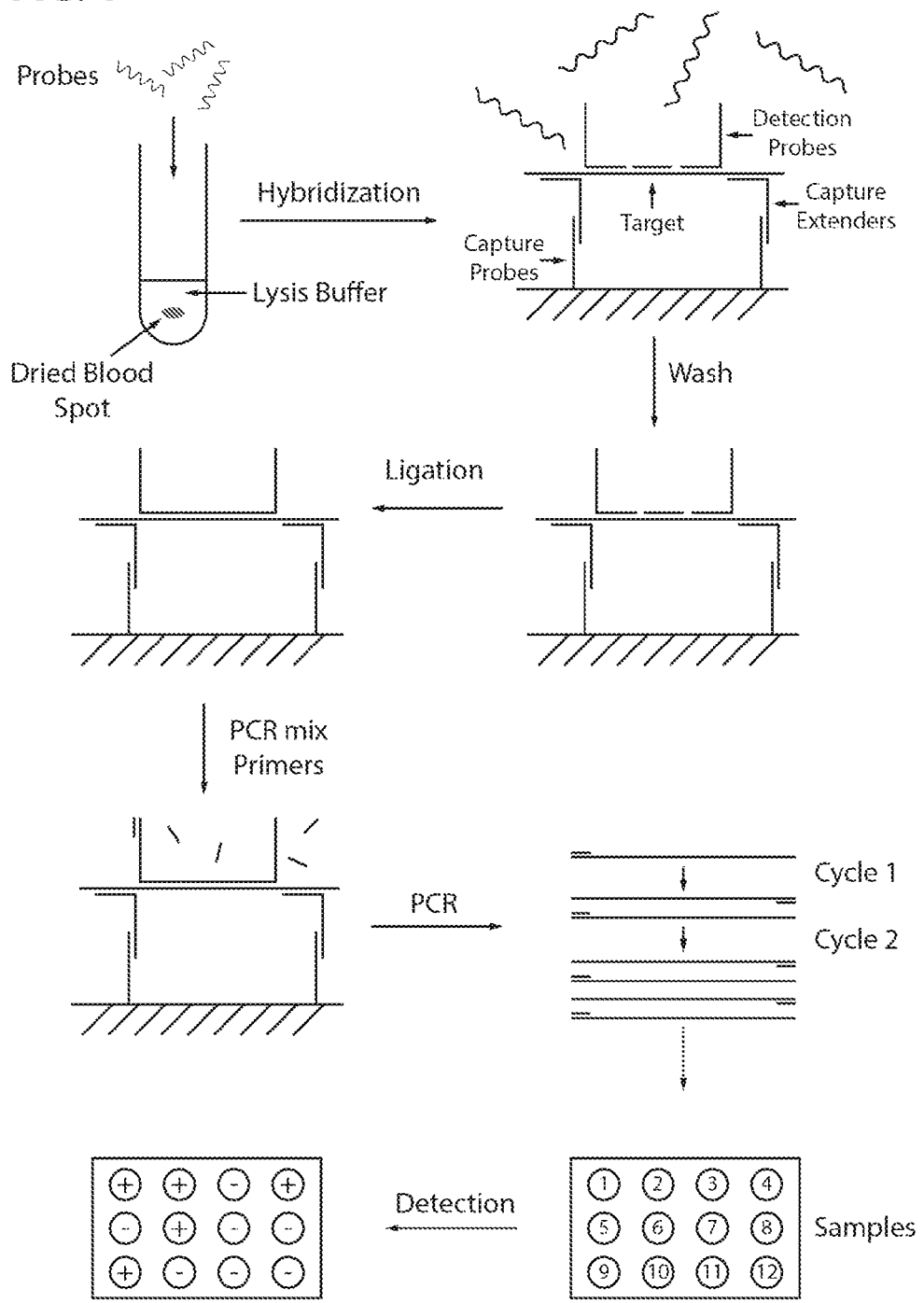
FIG. 1 shows a schematic of an exemplary method for using ligation-enabled PCR to detect the presence of a target nucleic acid in a biological sample.

The present invention provides simplified nucleic acid amplification and detection systems suitable for clinical assays of nucleic acids of interest in a sample, such as a biological sample. The method utilizes nucleic acid hybridization-based capture and amplification, such as ligation-based amplification, to directly detect nucleic acids in a biological sample, without the need for nucleic acid preparation. The methods are sensitive, efficient, and easily adaptable to users' needs, thus are particularly suitable in a clinical setting, especially when analyzing multiple biological samples simultaneously.

The methods of the present application represent a significant improvement over prior ligation-dependent amplification methods which rely on biotin-strepavidin interactions to anchor target nucleic acids to a solid support. See, e.g., Hsuih et al., J. Clin. Microbiol. 34(3): 501-7, 1996. Affinity between biotin and streptavidin is extraordinarily high and conjugation of the two is fast and irreversible at RNA/DNA hybridization temperatures (Anders et al., Electrophoresis 26(3): 501-510, 2005). On the other hand, hybridization between capture probes and target nucleic acid (such as RNA) is slow and may take up to more than 16 hours, especially when the target is scarce. As a consequence, capture probes with biotin will be anchored to the streptavidin-coated surface before they hybridize with target RNA. This leads to three consequences. First, capture probes will have lower capture efficiency when they are anchored to a surface compared with those in the solution phase. Second, since biotin-streptavidin conjugation is a sequence-independent process, the target specific capture probes will be anchored to the surface in a random fashion instead of in a configuration favorable to capture, and will not be able to capture the target efficiently due to steric effects. Third, since biotin and streptavidin interaction is irreversible, free capture probes bound to the surface will prevent the target/capture probe complex from binding to the surface. Consequently, the sensitivity of ligation-dependent PCR assay using biotin-streptavidin based capture is low (Hsuih et al., J. Clin. Microbiol. 34(3): 501-7, 1996) and the assay has not been widely used.

The present invention provides an alternative amplification system referred to as ligation-enabled PCR (LE-PCR) that utilizes nucleic acid hybridization to anchor the target nucleic acids to a solid support. Nucleic acid hybridization-based capture relies on annealing of complementary nucleic acid sequences, a reversible process, and when combined with ligation-based PCR has the potential to yield a highly selective and sensitive assay for the detection of dilute target nucleic acids by optimizing the hybridization stringency through varying parameters that include, but are not limited to, temperature, incubation time, washing, and the number and configuration of distinct target nucleic acid-specific probes. The methods are therefore significantly more sensitive and specific compared to prior methods, and lead to at least the following advantages: 1) suitability for clinical laboratory settings, 2) ability to detect small amounts of nucleic acids in biological samples, optionally without nucleic acid preparation, 3) ability to obtain controlled and consistent (standardizable) results, 4) ability to simultaneously detect multiple distinct target nucleic acids in biological samples, 5) ability to pool samples and retain detection sensitivity, and 6) reduced cost and technical skill required compared to presently available methods.

Further, the present method allows for easier automation and continuous processing of multiple samples. For example, multiple samples, regardless of source (e.g., human, livestock, plant, water) or type (e.g., blood, saliva, nasal swab, pharyngeal swab, cheek swab, urine, etc.) can be assayed in parallel. A different target nucleic acid can be detected in each of the samples that are being processed in parallel. Multiple target nucleic acids (such as from a single pathogen or from a plurality of different pathogens) can be detected simultaneously in each of the samples that are being processed in parallel.

Thus, the present application in one aspect provides a method of detecting (including sequencing) a target nucleic acid from a biological sample using ligation-based amplification coupled with nucleic acid hybridization-based target nucleic acid capture (LE-PCR). In another aspect, there is provided a method of detecting (including sequencing) a target nucleic acid from a biological sample using other known nucleic acid amplification techniques, such as PCR, LAMP and RCA, coupled with nucleic acid hybridization-based target nucleic acid capture. In another aspect, there is provided a method of detecting a pathogen in a biological sample using the methods described herein. Further provided are methods of diagnosing diseases and detecting genetic variations using the methods described herein. Also provided are kits and articles of manufacture useful for carrying out the methods described herein.

As used herein and in the appended claims, the singular forms "a," "an," and "the" include plural reference unless the context clearly indicates otherwise.

Reference to "about" a value or parameter herein includes (and describes) embodiments that are directed to that value or parameter per se. For example, description referring to "about X" includes description of "X."

Methods of the Present Invention

The present application provides methods of detecting a target nucleic acid in a biological sample comprising contacting the biological sample with detection probes, capture extenders and capture probes. Capture extenders each comprise a) a capturing sequence that is complementary to a region of the target nucleic acid; and b) an immobilizing sequence that is complementary to a sequence in a capture probe. The capture probes are bound to a solid support, thus immobilizing target nucleic acid hybridized to a capture extender's capturing sequence through hybridization of the bound capture probe with the capture extender's immobilizing sequence. Detection probes each comprise a sequence that is complementary to a region of the target nucleic acid, and may further comprise generic sequences that are not complementary to any regions of the target nucleic acid and comprise generic primer binding sites useful for amplification. Where a plurality of detection probes are provided that recognize a single target nucleic acid, detection probes hybridized to the target nucleic acid immobilized on the solid support can be ligated to form a single ligated detection sequence. Once ligated, the ligated detection sequence can be amplified and detected. Such methods allow biological samples to be processed without the need for purification of nucleic acids from the biological sample or the need for reverse transcription when the target nucleic acid is RNA. The detection probes can be hybridized to the target nucleic acids before or after the target nucleic acid is immobilized to a solid support. Alternatively, the hybridization of the detection probe and the immobilization reactions are carried out simultaneously.

"Biological sample" used herein refers to a sample derived from a biological source such as an animal, a plant, a food source, or an environmental source, and is also meant to include a sample derived from multiple biological sources.

"Nucleic acid" used herein includes both DNA (such as genomic DNA) and RNA (such as mRNA or rRNA).

"Contiguous" used herein when referring to regions of a nucleic acid means that the regions are non-overlapping and there is no more than about 500 bases between the different regions, e.g., contiguous regions of a nucleic acid may be separated by about any of 0, 50, 100, 150, 200, 250, 300, 350, 400, 450 or 500 bases. There may or may not be gaps between the contiguous regions. The contiguous regions are deemed "adjacent" to each other when there is no gap between the different regions. "Non-contiguous" used herein when referring to regions of a nucleic acid means that the regions are non-overlapping and they are separated by more than about 500 bases, e.g., non-contiguous regions of a nucleic acid may be separated by about any of 550, 750, 1000, 1500, 2000, 2500, 3000, 3500, 4000, 4500 or 5000 bases.

Thus, in some embodiments, there is provided a method of detecting a target nucleic acid in a sample comprising: a) capturing the target nucleic acid through a plurality of capture extenders, wherein each of the capture extenders comprises a capturing sequence that hybridizes to a region on the target nucleic acid and an immobilizing sequence that hybridizes to a capture probe conjugated to a solid support, thereby immobilizing the target nucleic acid to the solid support; b) contacting the target nucleic acid with a plurality of detection probes, wherein each of the plurality of detection probes comprises a sequence that hybridizes to a region on the target nucleic acid; c) ligating said plurality of detection probes to form a ligated detection sequence; d) amplifying said ligated detection sequence; and e) detecting (such as sequencing) the amplified ligated detection sequence. In some embodiments, the plurality of detection probes hybridize to contiguous regions of the target nucleic acid. Neighboring contiguous regions may be adjacent to each other (i.e., there is no gap between them), or may have a gap between them that is no more than about 500 bases. In some embodiments, the plurality of detection probes hybridize to adjacent regions of the target nucleic acid. In some embodiments, at least some of the plurality of detection probes hybridize to non-contiguous regions of the target nucleic acid. Neighboring non-contiguous regions are separated by more than about 500 bases. In some embodiments, the plurality of capture extenders hybridize to contiguous (such as adjacent) regions of the target nucleic acid. In some embodiments, at least some of the plurality of capture extenders hybridize to non-contiguous regions of the target nucleic acid. In some embodiments, at least some of the detection probes and capture extenders hybridize to contiguous (such as adjacent) regions of the target nucleic acid. In some embodiments, the capture extenders do not hybridize to any region between regions where the detection probes hybridize. In some embodiments, where the target nucleic acid has more than one strand, the capture extenders hybridize to the same strand of the target nucleic acid. In some embodiments, where the target nucleic acid has more than one strand, at least some of the capture extenders hybridize to different strands of the target nucleic acid. In some embodiments, step a) is carried out before step b), such that the target nucleic acid is first captured and immobilized to the solid support through the interaction of capture extenders hybridized to the target nucleic acid and capture probes bound to the solid support, followed by hybridization of detection probes to the bound target nucleic acid. In some embodiments, step a) is carried out after step b), such that a complex of target nucleic acid and hybridized detection probe is first formed, followed by capture and immobilization of the target nucleic acid/detection probe complex through the interaction of capture extenders hybridized to the target nucleic acid and capture probes bound to the solid support. In some embodiments, step a) and step b) are carried out concurrently, such that the target nucleic acid is allowed to hybridize with i) detection probes; ii) free capture extenders; and iii) immobilized capture extenders hybridized to bound capture probes. In some embodiments, the sample is a biological sample. In some embodiments, the biological sample is selected from the group consisting of a cell lysate, a tissue homogenate, a blood sample, a plasma sample, a serum sample, a dried blood spot, a blood clot, a nasal swab, a pharyngeal swab, a cheek swab, urine and saliva. In some embodiments the target nucleic acid is free in the biological sample, such as not within a cell. In some embodiments, the target nucleic acid is bound within cells in the biological sample, and the method further comprises lysis of the cells prior to steps a) and b). In some embodiments, the target nucleic acid is RNA. In some embodiments, the RNA is messenger RNA. In some embodiments, the RNA is ribosomal RNA, such as 18S rRNA. In some embodiments, the target nucleic acid is DNA, such as genomic DNA.

In some embodiments, there is provided a method of detecting a pathogen comprising a target nucleic acid in a biological sample comprising: a) capturing said target nucleic acid through a plurality of capture extenders, wherein each of the capture extenders comprises a capturing sequence that hybridizes to a region on the target nucleic acid and an immobilizing sequence that hybridizes to a capture probe conjugated to a solid support, thereby immobilizing the target nucleic acid to the solid support; b) contacting the target nucleic acid with a plurality of detection probes, wherein each of the plurality of detection probes comprises a sequence that hybridizes to a region on the target nucleic acid; c) ligating said plurality of detection probes to form a ligated detection sequence; d) amplifying said ligated detection sequence; and e) detecting (such as sequencing) the amplified ligated detection sequence, wherein the detection of the amplified ligated detection sequence is indicative of the presence of the pathogen in the biological sample. In some embodiments, the plurality of detection probes hybridize to contiguous regions of the target nucleic acid. In some embodiments, the plurality of detection probes hybridize to adjacent regions of the target nucleic acid. In some embodiments, at least some of the plurality of detection probes hybridize to non-contiguous regions of the target nucleic acid. In some embodiments, the plurality of capture extenders hybridize to contiguous (such as adjacent) regions of the target nucleic acid. In some embodiments, at least some of the plurality of capture extenders hybridize to non-contiguous regions of the target nucleic acid. In some embodiments, at least some of the detection probes and capture extenders hybridize to contiguous (such as adjacent) regions of the target nucleic acid. In some embodiments, the capture extenders do not hybridize to any region between regions where the detection probes hybridize. In some embodiments, where the target nucleic acid has more than one strand, the capture extenders hybridize to the same strand of the target nucleic acid. In some embodiments, where the target nucleic acid has more than one strand, at least some of the capture extenders hybridize to different strands of the target nucleic acid. In some embodiments, step a) is carried out before step b). In some embodiments, step a) is carried out after step b). In some embodiments, step a) and step b) are carried out concurrently. In some embodiments, the biological sample is selected from the group consisting of a cell lysate, a tissue homogenate, a blood sample, a dried blood spot, a blood clot, a plasma sample, a serum sample, a nasal swab, a pharyngeal swab, a cheek swab, urine and saliva. In some embodiments the target nucleic acid is free in the biological sample, such as not within a cell. In some embodiments, the target nucleic acid is bound within cells in the biological sample, and the method further comprises lysis of the cells prior to steps a) and b). In some embodiments, the target nucleic acid is RNA. In some embodiments, the RNA is messenger RNA. In some embodiments, the RNA is ribosomal RNA, such as 18S rRNA. In some embodiments, the target nucleic acid is DNA, such as genomic DNA.

In some embodiments, there is provided a method of diagnosing a disease in an individual caused by a pathogen comprising a target nucleic acid comprising: a) capturing said target nucleic acid through a plurality of capture extenders, wherein each of the capture extenders comprises a capturing sequence that hybridizes to a region on the target nucleic acid and an immobilizing sequence that hybridizes to a capture probe conjugated to a solid support, thereby immobilizing the target nucleic acid to the solid support; b) contacting the target nucleic acid with a plurality of detection probes, wherein each of the plurality of detection probes comprises a sequence that hybridizes to a region on the target nucleic acid; c) ligating said plurality of detection probes to form a ligated detection sequence; d) amplifying said ligated detection sequence; and e) detecting (such as sequencing) said amplified ligated detection sequence, wherein the detection of the amplified ligated detection sequence is indicative of a positive diagnosis of the disease in the individual. In some embodiments, the plurality of detection probes hybridize to contiguous regions of the target nucleic acid. In some embodiments, the plurality of detection probes hybridize to adjacent regions of the target nucleic acid. In some embodiments, at least some of the plurality of detection probes hybridize to non-contiguous regions of the target nucleic acid. In some embodiments, the plurality of capture extenders hybridize to contiguous (such as adjacent) regions of the target nucleic acid. In some embodiments, at least some of the plurality of capture extenders hybridize to non-contiguous regions of the target nucleic acid. In some embodiments, at least some of the detection probes and capture extenders hybridize to contiguous (such as adjacent) regions of the target nucleic acid. In some embodiments, the capture extenders do not hybridize to any region between regions where the detection probes hybridize. In some embodiments, where the target nucleic acid has more than one strand, the capture extenders hybridize to the same strand of the target nucleic acid. In some embodiments, where the target nucleic acid has more than one strand, at least some of the capture extenders hybridize to different strands of the target nucleic acid. In some embodiments, step a) is carried out before step b). In some embodiments, step a) is carried out after step b). In some embodiments, step a) and step b) are carried out concurrently. In some embodiments, the biological sample is selected from the group consisting of a cell lysate, a tissue homogenate, a blood sample, a dried blood spot, a blood clot, a plasma sample, a serum sample, a nasal swab, a pharyngeal swab, a cheek swab, urine and saliva. In some embodiments the target nucleic acid is free in the biological sample, such as not within a cell. In some embodiments, the target nucleic acid is bound within cells in the biological sample, and the method further comprises lysis of the cells prior to steps a) and b). In some embodiments, the target nucleic acid is RNA. In some embodiments, the RNA is messenger RNA. In some embodiments, the RNA is ribosomal RNA, such as 18S rRNA. In some embodiments, the target nucleic acid is DNA, such as genomic DNA.

In some embodiments, there is provided a method of diagnosing a disease in an individual associated with an abnormal target nucleic acid (such as circulating tumor nucleic acid or prenatal nucleic acid in a body fluid sample) comprising: a) capturing said target nucleic acid through a plurality of capture extenders, wherein each of the capture extenders comprises a capturing sequence that hybridizes to a region on the target nucleic acid and an immobilizing sequence that hybridizes to a capture probe conjugated to a solid support, thereby immobilizing the target nucleic acid to the solid support; b) contacting the target nucleic acid with a plurality of detection probes, wherein each of the plurality of detection probes comprises a sequence that hybridizes to a region on the target nucleic acid; c) ligating said plurality of detection probes to form a ligated detection sequence; d) amplifying said ligated detection sequence; and e) detecting (such as sequencing) said amplified ligated detection sequence, wherein the detection of the amplified ligated detection sequence is indicative of a positive diagnosis of the disease in the individual. In some embodiments, the plurality of detection probes hybridize to contiguous regions of the target nucleic acid. In some embodiments, the plurality of detection probes hybridize to adjacent regions of the target nucleic acid. In some embodiments, at least some of the plurality of detection probes hybridize to non-contiguous regions of the target nucleic acid. In some embodiments, the plurality of capture extenders hybridize to contiguous (such as adjacent) regions of the target nucleic acid. In some embodiments, at least some of the plurality of capture extenders hybridize to non-contiguous regions of the target nucleic acid. In some embodiments, at least some of the detection probes and capture extenders hybridize to contiguous (such as adjacent) regions of the target nucleic acid. In some embodiments, the capture extenders do not hybridize to any region between regions where the detection probes hybridize. In some embodiments, where the target nucleic acid has more than one strand, the capture extenders hybridize to the same strand of the target nucleic acid. In some embodiments, where the target nucleic acid has more than one strand, at least some of the capture extenders hybridize to different strands of the target nucleic acid. In some embodiments, step a) is carried out before step b). In some embodiments, step a) is carried out after step b). In some embodiments, step a) and step b) are carried out concurrently. In some embodiments, the biological sample is selected from the group consisting of a cell lysate, a tissue homogenate, a blood sample, a dried blood spot, a blood clot, a plasma sample, a serum sample, a nasal swab, a pharyngeal swab, a cheek swab, urine and saliva. In some embodiments the target nucleic acid is free in the biological sample, such as not within a cell. In some embodiments, the target nucleic acid is bound within cells in the biological sample, and the method further comprises lysis of the cells prior to steps a) and b). In some embodiments, the target nucleic acid is RNA. In some embodiments, the RNA is messenger RNA. In some embodiments, the RNA is ribosomal RNA, such as 18S rRNA. In some embodiments, the target nucleic acid is DNA, such as genomic DNA.

In some embodiments, there is provided a method of diagnosing a disease in an individual by detecting a genetic variation in the individual comprising: a) capturing a target nucleic acid comprising the genetic variation from a biological sample of the individual through a plurality of capture extenders, wherein each of the capture extenders comprises a capturing sequence that hybridizes to a region on the target nucleic acid and an immobilizing sequence that hybridizes to a capture probe conjugated to a solid support, thereby immobilizing the target nucleic acid to the solid support; b) contacting the target nucleic acid with a plurality of detection probes, wherein each of the plurality of detection probes comprises a sequence that hybridizes to a region on the target nucleic acid, and wherein at least one of the detection probes is a variation-specific detection probe which preferentially hybridizes to a region on the target nucleic acid comprising all or a portion of the variation; c) ligating said plurality of detection probes to form a ligated detection sequence; d) amplifying said ligated detection sequence; and e) detecting the amplified ligated detection sequence, wherein the detection of the amplified ligated detection sequence is indicative of a positive diagnosis of the disease in the individual. In some embodiments, the variation-specific detection probe hybridizes to a region on the target nucleic acid comprising all or a portion of the variation but not a corresponding region not comprising all or a portion of the variation. In some embodiments, the variation-specific detection probe hybridizes to a region on the target nucleic acid comprising all or a portion of the variation at least about 10×, 20×, 30×, 40×, 50×, 100×, 150×, 200×, 300×, 400×, 500×, or more fold stronger than to a corresponding region not comprising all or a portion of the variation. In some embodiments, the variation is, inter alia, a mutation or a single nucleotide polymorphism (SNP). In some embodiments, both the variation-specific detection probe that hybridizes to a region on the target nucleic acid comprising all or a portion of the variation and a corresponding wild-type-specific probe that hybridizes to a region on the target nucleic acid not comprising all or a portion of the variation are present, such that the wild-type-specific detection probe will inhibit the variation-specific detection probe from hybridizing to the region not comprising all or a portion of the variation. The wild-type-specific detection probe is not phosphorylated at its 5' end while the variation-specific probe is phosphorylated at its 5' end, such that in the subsequent ligation reaction a wild-type-specific detection probe hybridized to the target nucleic acid cannot be ligated with an adjacent detection probe, preventing the formation of a ligated detection sequence and subsequent amplification of said ligated detection sequence from a target nucleic acid not comprising the variation. In some embodiments, the plurality of detection probes hybridize to contiguous regions of the target nucleic acid. In some embodiments, the plurality of detection probes hybridize to adjacent regions of the target nucleic acid. In some embodiments, at least some of the plurality of detection probes hybridize to non-contiguous regions of the target nucleic acid. In some embodiments, the plurality of capture extenders hybridize to contiguous (such as adjacent) regions of the target nucleic acid. In some embodiments, at least some of the plurality of capture extenders hybridize to non-contiguous regions of the target nucleic acid. In some embodiments, at least some of the detection probes and capture extenders hybridize to contiguous (such as adjacent) regions of the target nucleic acid. In some embodiments, the capture extenders do not hybridize to any region between regions where the detection probes hybridize. In some embodiments, where the target nucleic acid has more than one strand, the capture extenders hybridize to the same strand of the target nucleic acid. In some embodiments, where the target nucleic acid has more than one strand, at least some of the capture extenders hybridize to different strands of the target nucleic acid. In some embodiments, step a) is carried out before step b). In some embodiments, step a) is carried out after step b). In some embodiments, step a) and step b) are carried out concurrently. In some embodiments, the biological sample is selected from the group consisting of a cell lysate, a tissue homogenate, a blood sample, a dried blood spot, a blood clot, a plasma sample, a serum sample, a nasal swab, a pharyngeal swab, a cheek swab, urine and saliva. In some embodiments the target nucleic acid is free in the biological sample, such as not within a cell. In some embodiments, the target nucleic acid is bound within cells in the biological sample, and the method further comprises lysis of the cells prior to steps a) and b). In some embodiments, the target nucleic acid is RNA. In some embodiments, the RNA is messenger RNA. In some embodiments, the RNA is ribosomal RNA, such as 18S rRNA. In some embodiments, the target nucleic acid is DNA, such as genomic DNA.

In some embodiments, there is provided a method of diagnosing a disease in an individual by detecting a genetic variation in the individual comprising: a) capturing a target nucleic acid comprising the genetic variation from a biological sample of the individual through a plurality of capture extenders, wherein each of the capture extenders comprises a capturing sequence that hybridizes to a region on the target nucleic acid and an immobilizing sequence that hybridizes to a capture probe conjugated to a solid support, thereby immobilizing the target nucleic acid to the solid support; b) contacting the target nucleic acid with a plurality of detection probes, wherein each of the plurality of detection probes comprises a sequence that hybridizes to a region on the target nucleic acid, wherein the target nucleic acid comprises a gap region between two detection targeting sequences that is not hybridizable to any of the detection probes, and wherein the gap region comprises the variation; c) filling in the gap between two detection probes separated by the gap region comprising the variation; d) ligating said plurality of detection probes to form a ligated detection sequence comprising the variation; e) amplifying said ligated detection sequence; and f) detecting the variation in the amplified ligated detection sequence, wherein the presence of the variation in the amplified ligated detection sequence is indicative of a positive diagnosis of the disease in the individual. In some embodiments, the variation is, inter alia, a mutation or a SNP. In some embodiments, the detection is carried out by sequencing the amplified ligated detection sequence. In some embodiments, the detection is carried out by performing single-base extension. In some embodiments, the detection is carried out by MALDI-TOF. In some embodiments, the gap filling is carried out by a DNA polymerase or reverse transcriptase. In some embodiments, the plurality of detection probes hybridize to contiguous regions of the target nucleic acid. In some embodiments, at least some of the plurality of detection probes hybridize to non-contiguous regions of the target nucleic acid. In some embodiments, the plurality of capture extenders hybridize to contiguous (such as adjacent) regions of the target nucleic acid. In some embodiments, at least some of the plurality of capture extenders hybridize to non-contiguous regions of the target nucleic acid. In some embodiments, at least some of the detection probes and capture extenders hybridize to contiguous (such as adjacent) regions of the target nucleic acid. In some embodiments, the capture extenders do not hybridize to any region between regions where the detection probes hybridize. In some embodiments, where the target nucleic acid has more than one strand, the capture extenders hybridize to the same strand of the target nucleic acid. In some embodiments, where the target nucleic acid has more than one strand, at least some of the capture extenders hybridize to different strands of the target nucleic acid. In some embodiments, the gap-filling is carried out by primer extension. In some embodiments, step a) is carried out before step b). In some embodiments, step a) is carried out after step b). In some embodiments, step a) and step b) are carried out concurrently. In some embodiments, the biological sample is selected from the group consisting of a cell lysate, a tissue homogenate, a blood sample, a plasma sample, a serum sample, a dried blood spot, a blood clot, a nasal swab, a pharyngeal swab, a cheek swab, urine and saliva. In some embodiments the target nucleic acid is free in the biological sample, such as not within a cell. In some embodiments, the target nucleic acid is bound within cells in the biological sample, and the method further comprises lysis of the cells prior to steps a) and b). In some embodiments, the target nucleic acid is RNA. In some embodiments, the RNA is messenger RNA. In some embodiments, the RNA is ribosomal RNA, such as 18S rRNA. In some embodiments, the target nucleic acid is DNA, such as genomic DNA.

In some embodiments, the target nucleic acid is within cells of a biological sample, and lysis of the cells may be carried out using any method known in the art. In some embodiments, lysis is carried out by adding a sufficient volume of a lysis solution to the biological sample in a reaction vessel. The lysis solution may be any solution known in the art used for lysing cells, including, for example, solutions comprising: a) salts to regulate the acidity and osmolarity of the lysate; and b) detergents, such as Triton X-100 and SDS, to break up membrane structures. In some embodiments, the lysis solution is a solution comprising about 10 to about 20 mM Tris-HCl (such as about 15 mM Tris-HCl), about 130 to about 170 mM NaCl (such as about 150 mM NaCl), about 0.5 to about 2 mM EDTA (such as about 1 mM EDTA), and about 0.5 to about 2% Triton X-100 (such as about 1% Triton X-100). In some embodiments, the lysis solution further comprises about 0.5 to about 2 mM EGTA (such as about 1 mM EGTA). In some embodiments, the lysis solution further comprises about 0.5 to about 3 mg/ml proteinase K (such as about 1.5 mg/ml proteinase K). In some embodiments, the lysis solution further comprises a probe mixture that comprises detection probes and capture extenders. In some embodiments the lysis reaction is carried out in a reaction vessel, including, but not limited to, a centrifuge tube (such as a microcentrifuge tube) or a multiwell plate. In some embodiments, the lysis reaction is incubated at a temperature of about 37 to about 65° C. (such as about any of 50, 51, 52, 53, 54, 55, 56, 57, 58, 59 or 60° C.). In some embodiments, the lysis reaction is incubated for about 10 to about 60 minutes (such as about any of 20, 25, 30, 35 or 40 minutes). In some embodiments, the lysis reaction is carried out with vigorous shaking.

The solid support on which the capture probes are immobilized may be particulate or be a solid surface, for example the wall surface of any of a variety of containers, e.g., centrifugal tubes, columns, multiwell plate wells, filters, tubing, etc. The solid surface can also be the surface of a paper, e.g., a nitrocellulose paper, or the surface of a membrane, e.g., a nylon membrane. In some embodiments, multiwell plate wells are a preferred solid surface. In some embodiments, when particles are used, they will be of a size in the range of about 0.4 to about 200 microns, more usually from about 0.8 to about 10 microns. The particles may comprise any convenient material, such as iron oxide, various polymers, or glass. In some embodiments, the particles are beads selected from the group consisting of magnetic beads, Luminex microspheres and Illumina beads. Capture probes may be stably attached to the solid support through functional groups by any method known in the art. In some embodiments, when using beads for multiplex target amplification, beads are designed to capture different target nucleic acids and each bead is bound with only one capture probe variant having a distinct sequence, and the capture extenders for different target nucleic acids contain different immobilization sequences that are complementary to a sequence present in only one of the distinct capture probe variants, such that one target nucleic acid will not simultaneously be immobilized onto two or more beads bound with different capture probes, nor will two or more different target nucleic acids be immobilized onto a single bead, thus preventing the reduction in immobilization efficiency resulting from either of these situations. Similarly, multiwell plates can be used to capture different target nucleic acids via different capture probes.

In some embodiments, hybridization is carried out in an aqueous medium, particularly a buffered aqueous medium, which may include various additives. In some embodiments, the additives which may be employed include low concentrations of detergent (about 0.1 to about 1%), salts, e.g., sodium citrate (about 0.017 to about 0.170 M), Ficoll, polyvinylpyrrolidine, carrier nucleic acids, carrier proteins, etc. In some embodiments, non-aqueous solvents may be added to the aqueous medium, such as dimethylformamide, dimethylsulfoxide, alcohols, and formamide. In some embodiments, these other solvents will be present in amounts ranging from about 2 to about 50%. In some embodiments, hybridization is carried out at about 45 to about 65° C. (such as about any of 50, 51, 52, 53, 54, 55, 56, 57, 58, 59 or 60° C.). In some embodiments, the hybridization is carried out for about 4 to about 24 hours (such as about any of 10, 12, 14, 16, 18, or 20 hours). The stringency of the hybridization may be controlled to achieve a desired selectivity and/or sensitivity by controlling, inter alia, temperature, salt concentration, solvent system, incubation time and the like. Thus in some embodiments, depending upon the length and nature of the sequence of interest, the stringency will be varied. Generally, when a variation-specific detection probe is required for detecting a variation in the target nucleic acid, the stringency of the hybridization conditions is such that a single mismatch between a region of the target nucleic acid and the sequence of the detection probe designed to be complementary to the region of the target nucleic acid would prevent hybridization. Alternatively, less stringent hybridization reaction conditions can be used, for example when a universal, degenerate detection probe is used to hybridize to multiple regions of the target nucleic acid.

In some embodiments, hybridization is carried out in a hybridization vessel. In some embodiments, where there is a lysis step, the hybridization vessel can be the same reaction vessel used for lysis. In some embodiments, where there is a lysis step, the hybridization vessel is not the reaction vessel used for lysis, and the lysate is transferred from the reaction vessel used for lysis to the hybridization vessel. In some embodiments, the hybridization vessel is a multiwell plate (including, but not limited to, a 96-well plate). In some embodiments, surfaces of the hybridization vessel, such as the wells of a multiwell plate, are pre-conjugated with capture probes that can hybridize to the capture extenders. In some embodiments, the hybridization vessel is a centrifuge tube (such as a microcentrifuge tube). In some embodiments, the hybridization vessel is not pre-conjugation with capture probes, and a particulate solid support, such as beads or microspheres, is pre-conjugated with capture probes that can hybridize to the capture extenders and added to the hybridization vessel.

In some embodiments, unbound components of the hybridization step, including unbound probes and nucleic acids, are separated from hybridized complexes bound to the solid support. In some embodiments, the unbound components of the hybridization step are separated by washing the bound hybridized complexes. In some embodiments, washing the bound hybridized complexes comprises any of about 1 to about 5 wash steps with an appropriate wash solution, wherein the supernatant may be isolated or discarded after each wash step. The conditions of a wash step can be modified to control the level of selectivity and/or sensitivity for the bound hybridized complexes by any method known in the art, which can include, inter alia, modifying the stringency of the wash solution, modifying the incubation time with the wash solution, modifying the temperature under which the wash step is carried out, and/or modifying the agitation applied during the wash step. The wash solution of a wash step can be any solution known in the art useful for post-hybridization washing to remove unbound components. In some embodiments, the wash solution comprises any of about 0.1 to about 2×SSC (such as about any of 0.1, 0.2, 0.5, 1, or 2×SSC). In some embodiments, at each successive wash step the stringency of the wash solution remains the same, e.g., the first, second and third wash steps are performed with wash solutions comprising about 0.1× SSC. In some embodiments, at each successive wash step the stringency of the wash solution is increased, e.g., the first wash solution comprises about 2×SSC, the second wash solution comprises about 1×SSC and the third wash solution comprises about 0.1×SSC. The stringency of the wash solution can be controlled using any method known in the art, such as, for example, varying the salt concentration of the wash solution.

The procedure used in the wash steps of the present invention will vary depending upon the nature of the solid support. In some embodiments, where the solid support is a surface, such as the surface of a multiwell plate well, the supernatant may be isolated or discarded and the surface washed as described above. In some embodiments, where the solid support is a particle, the particles may be washed as described above, wherein centrifugation, filtration or partitioning to the side of a vessel under the influence of an external magnetic field will provide for separation of the particles from the supernatant, allowing for isolating or discarding of the supernatant.

In some embodiments, following capture of complexes comprising target nucleic acid and hybridized detection probes on the solid support, and separation of unbound reaction components, adjacent 5' and 3' ends of the hybridized detection probes are ligated together using a ligating agent to form a single nucleic acid molecule comprising the hybridized detection probes, referred to herein as a ligated detection sequence. In some embodiments, the ligating agent may be an enzyme, e.g., a DNA or RNA ligase, or a chemical joining agent, e.g., cyanogen bromide or a carbodiimide (Sokolova et al., FEBS Lett. 232:153-155, 1988). Preferred DNA ligases include T4 DNA ligase. The presence of the ligated detection sequence indicates the presence of target nucleic acid in the sample. In some embodiments, the ligated detection sequence serves as the template for any of various amplification systems, such as PCR, LAMP or SDA. Any of the detection probes which remain unligated after treatment will not be amplified in subsequent steps in the method.

In some embodiments, the 5' detection probe and any internal detection probes are provided with phosphorylated 5' ends, and ligation can be carried out without additional steps. In some embodiments, the detection probes are unphosphorylated, and the ligation step further comprises treatment with an enzyme capable of phosphorylating the 5' ends of the detection probes. The phosphorylation of the detection probes can be carried out using any method known in the art. In some embodiments, the phosphorylating enzyme is a kinase, such as T4 polynucleotide kinase. In some embodiments, the phosphorylation reaction is carried out prior to ligation but after hybridization. In some embodiments, the phosphorylation step is carried out at the same time as ligation.

In some embodiments, no enzymes are used for the ligation of the detection probes, and the ligation is carried out automatically. The 3' ends of the 3' detection probe and any internal detection probes and the 5' ends of the 5' detection probe and any internal detection probes may contain appropriate chemical modifications, such as a chemically attacking group and a leaving group, respectively, such that the ligating step is carried out chemically by forming covalent bonds between adjacent detection probes, without the use of an enzyme. (Y. Xu, N. B. Karalkar, E. T. Kool. "Nonenzymatic Autoligation in Direct Three-Color Detection of RNA and DNA Point Mutations" Nat. Biotech. 2001, 19, 148-152.)

In some embodiments, where the hybridized detection probes comprise sequences that are complementary to non-adjacent regions of the target nucleic acid, the ligation step further comprises treatment with an enzyme capable of filling in the gaps between non-adjacent detection probes. The gap-filling reaction can be carried out using any method known in the art. In some embodiments, the gap-filling enzyme is a DNA polymerase or a reverse transcriptase, depending on whether the target nucleic acid is DNA or RNA, respectively. In some embodiments, the gaps are filled prior to ligation. In some embodiments, the gaps are filled at the same time as ligation.

The ligated detection sequence can be detected by any method known in the art, including, inter alia, real-time PCR or an equivalent thereof, gel electrophoresis, mass spectroscopy-based detection or sequencing. In some embodiments, the ligated detection sequence is amplified by any method known in the art. In some embodiments, the ligated detection sequence is amplified by PCR to generate a PCR product. In some embodiments, the PCR product is detected by any method known in the art. In some embodiments, the ligated detection sequence is amplified and detected using real-time quantitative polymerase chain reaction (RT-qPCR). In some embodiments, the ligated detection sequence (with or without amplification) is detected by sequencing.

In some embodiments, when PCR-based technique are used for amplification, PCR primers are provided, namely, a first primer complementary to a region on the 5' detection probe, this region being referred to herein as a 5' primer binding site, and a second primer corresponding to a region on the 3' detection probe, this region being referred to herein as a 3' primer binding site. In some embodiments, the primer binding sites on the 5' and 3' detection probes are part of the sequence hybridizable to the target nucleic acid. Alternatively, in some embodiments the 3' end of at least one 5' detection probe contains a generic 3' tail sequence and the 5' end of at least one 3' detection probe contains a generic 5' tail sequence, these generic tail sequences being useful for designing universal PCR primers. Universal PCR primers are particularly useful when multiple target nucleic acids are being detected. For example, two sets of probes, each set comprising: a) detection probes comprising generic 3' and 5' tails comprising generic 5' and 3' primer binding sites, respectively; and b) capture extenders; wherein the detection probes and capture extenders of the first set are specific for HIV-1 and the detection probes and capture extenders of the second set are specific for HCV, can be used together in any of the methods of the present invention, with only one pair of generic PCR primers used to amplify each of a ligated detection sequence specific for either HIV-1 or HCV.

Thus, in some embodiments, there is provided a method for detecting a plurality of target nucleic acids in a sample comprising: a) capturing one of the plurality of target nucleic acids through a plurality of capture extenders, wherein each of the capture extenders comprises a capturing sequence that hybridizes to a region on the target nucleic acid and an immobilizing sequence that hybridizes to a capture probe conjugated to a solid support, thereby immobilizing the target nucleic acid to the solid support; b) contacting one of the plurality of target nucleic acids with a plurality of detection probes comprising a first primer binding site and a second primer binding site, wherein each of the plurality of detection probes comprises a sequence that hybridizes to a region on the target nucleic acid; c) carrying out steps a) and b) for each of the plurality of target nucleic acids; d) ligating the plurality of detection probes to form a plurality of ligated detection sequences specific to each of the plurality of target nucleic acids; e) amplifying the plurality of ligated detection sequences; and f) detecting the plurality of amplified ligated detection sequences. In some embodiments, each plurality of detection probes specific for each of the plurality of target nucleic acids comprises the same first primer binding site and the same second primer binding site, and the amplification step is carried out using PCR with a primer pair corresponding to the first and second primer binding sites. This method, and variations of this method used to detect a plurality of target nucleic acids, is designated as multiplex LE-PCR. In some embodiments, for each of the target nucleic acids, the plurality of detection probes corresponding to the target nucleic acid hybridize to contiguous regions of the target nucleic acid. In some embodiments, for each of the target nucleic acids, the plurality of detection probes corresponding to the target nucleic acid hybridize to adjacent regions of the target nucleic acid. In some embodiments, for each of the target nucleic acids, at least some of the plurality of detection probes corresponding to the target nucleic acid hybridize to non-contiguous regions of the target nucleic acid. In some embodiments, for each of the target nucleic acids, the plurality of capture extenders corresponding to the target nucleic acid hybridize to contiguous (such as adjacent) regions of the target nucleic acid. In some embodiments, for each of the target nucleic acids, at least some of the plurality of capture extenders corresponding to the target nucleic acid hybridize to non-contiguous regions of the target nucleic acid. In some embodiments, for each of the target nucleic acids, at least some of the detection probes and capture extenders corresponding to the target nucleic acid hybridize to contiguous (such as adjacent) regions of the target nucleic acid. In some embodiments, for each of the target nucleic acids, the capture extenders corresponding to the target nucleic acid do not hybridize to any region between regions where the detection probes corresponding to the target nucleic acid hybridize. In some embodiments, step a) is carried out before step b). In some embodiments, step a) is carried out after step b). In some embodiments, step a) and step b) are carried out concurrently. In some embodiments, the sample is a biological sample. In some embodiments, the biological sample is selected from the group consisting of a cell lysate, a tissue homogenate, a blood sample, a dried blood spot, a blood clot, a plasma sample, a serum sample, a nasal swab, a pharyngeal swab, a cheek swab, urine and saliva. In some embodiments the target nucleic acid is free in the biological sample, such as not within a cell. In some embodiments, the target nucleic acid is bound within cells in the biological sample, and the method further comprises lysis of the cells prior to steps a) and b). In some embodiments, the target nucleic acid is RNA. In some embodiments, the RNA is messenger RNA. In some embodiments, the RNA is ribosomal RNA, such as 18S rRNA. In some embodiments, the target nucleic acid is DNA, such as genomic DNA.

In some embodiments of multiplex LE-PCR as described above, each of the capture extenders comprises a same generic immobilizing sequence and each of the capture probes comprises a same generic region that hybridizes with the generic immobilizing sequence, allowing for amplification and detection of ligated detection sequences specific for any of the target nucleic acids. In some embodiments of multiplex LE-PCR, for each of the target nucleic acids, each of the plurality of capture extenders specific for the target nucleic acid comprises the same immobilizing sequence, which is different than the immobilizing sequence of any of the other capture extenders specific for different target nucleic acids, and for each immobilizing sequence there is provided a capture probe comprising a region that hybridizes with the immobilizing sequence, wherein each of the distinct capture probes is attached only to a specific solid support that can be separated from the solid supports to which the other capture probes are attached. For example, in some embodiments of multiplex LE-PCR, a plurality of capture extenders specific for a target nucleic acid A each comprise immobilizing sequence A, a plurality of capture extenders specific for a target nucleic acid B each comprise immobilizing sequence B, capture probe A can hybridize with immobilizing sequence A and is attached only to beads of type A, capture probe B can hybridize with immobilizing sequence B and is attached only to beads of type B, and beads of type A can be separated from beads of type B by any method known in the art, such as, inter alia, by flow cytometry, such that amplification and detection of a ligated detection sequence specific to target nucleic acid A can be carried out separately from amplification and detection of a ligated detection sequence specific to target nucleic acid B, thus allowing for the detection of each of the target nucleic acids from a single sample individually, while still requiring the use of only one generic PCR primer pair.

In prior methods of PCR amplification of a target nucleic acid, attempts to detect multiple targets with multiple primer pairs in a single reaction vessel have been limited by varying primer efficiencies and competition among primer pairs. In contrast, in a preferred embodiment of the present invention, detection probes are provided such that a plurality of ligated detection sequences, each corresponding to different target nucleic acids, are generated, wherein each ligated detection sequence comprises the same generic 3' and 5' primer binding sites. In some embodiments of multiplex LE-PCR, for each of the plurality of target nucleic acids, the plurality of detection probes corresponding to the target nucleic acid comprise the same generic 5' and 3' primer binding sites. Thus multiple sets of detection probes and capture extenders, each set specific for one of a plurality of target nucleic acids, may be used, but only one pair of generic PCR primers is needed to amplify the ligated detection probes corresponding to each of the plurality of target nucleic acids. By varying the length of the target specific regions of the detection probes, amplified PCR products corresponding to a particular target can be identified by size. Taqman probes specific to different target nucleic acids can also be used in RT-qPCR to detect the presence of the corresponding target nucleic acid in a multiplex LE-PCR assay.

In some embodiments there is provided a method of sequencing a plurality of target nucleic acids, comprising: a) performing multiplex LE-PCR capture as described above, wherein for each target nucleic acid, the detection targeting sequences of the plurality of detection probes corresponding to the target nucleic acid comprise a gap; b) filling in any gaps between detection probes bound to target nucleic acids with a polymerase; c) ligating the bound detection probes to form ligated detection sequences; d) amplifying the ligated detection sequences with a pair of universal PCR primers, wherein the primers have additional 5' index sequences compatible with next-generation sequencing (NGS) procedures, resulting in a mixture of amplified ligated detection sequences corresponding to each of the plurality of target nucleic acids; and e) subjecting the mixture to sequencing (e.g. Illumina NGS procedures). In some embodiments, the amount of each target in the mixture is determined by measuring "digital counts" of the target sequence. In some embodiments, any sequence variants are identified by comparing sequence reads to reference sequences. In some embodiments, MALDI-TOF detection is used to detect the presence of known sequence variants, for example by subjecting the mixture to one round of a single-base-extension reaction using ddNTP and a primer that binds just upstream of the variance site and detecting the extended product using a MALDI-TOF mass spectrometer.

In some embodiments, the multiple sets of detection probes and capture extenders may target, for example, all strains of a particular pathogen, e.g. the Hepatitis C Virus (HCV), and probes may be tailored to detect and further identify individual HCV genotypes of the pathogen (e.g. HCV).

In some embodiments, the multiple sets of detection probes and capture extenders may target, for example, all exons of a particular gene whose mutations may be of importance to the diagnosis, treatment and prognosis of a disease, e.g. cancer. In some embodiments, the multiple sets of detection probes and capture extenders may target all known sequence variants of a set of candidate genes whose sequence variation may be of importance to the diagnosis, treatment and prognosis of a disease, e.g. cancer.

In some embodiments, a detection probe is provided such that the ligated detection sequence forms a circularized nucleic acid molecule, wherein the detection probe has 5' and 3' ends that are complementary to contiguous regions of the target nucleic acid, and this detection probe is referred to herein as a circularizing detection probe. In some embodiments, when using a PCR-based technique for amplification with a circularizing detection probe, two primers are provided, a first primer being complementary to a first primer binding site of the circularizing detection probe and a second primer having the sequence of a second primer binding site located between the first primer binding site and the 3' end of the circularizing detection probe. In some embodiments, a primer pair comprising a first primer and a second primer as described above is designed to be generic, wherein the primers correspond to generic regions of the circularizing detection probe outside the regions of complementary between the circularizing detection probe and the target nucleic acid, such that the primer pair may be used for amplification of all ligated detection sequences of the present invention resulting from ligation of a circularizing detection probe comprising generic primer binding sites corresponding to the generic primer pair, irrespective of the sequence of the target nucleic acid. In some embodiments, the circularized ligated detection sequence is amplified using Rolling Circle Amplification (RCA), wherein the RCA-amplified product will remain attached to the target nucleic acid-capture extender-capture probe complex bound to the solid support, allowing the RCA-amplified product to be separately detected.

In some embodiments of any of the methods described herein, the plurality of detection probes is replaced with a single detection probe, the ligating step is omitted, and the detection probe is amplified and detected by any means known in the art, such as PCR, LAMP and RCA. Thus, for example, in some embodiments there is provided a method of detecting a target nucleic acid in a sample comprising: a) capturing the target nucleic acid through a plurality of capture extenders, wherein each of the capture extenders comprises a capturing sequence that hybridizes to a region on the target nucleic acid and an immobilizing sequence that hybridizes to a capture probe conjugated to a solid support, thereby immobilizing the target nucleic acid to the solid support; b) contacting the target nucleic acid with a detection probe comprising a sequence that hybridizes to a region on the target nucleic acid; c) amplifying said detection probe; and d) detecting (such as sequencing) the amplified detection probe. In some embodiments, the plurality of capture extenders hybridize to contiguous (such as adjacent) regions of the target nucleic acid. In some embodiments, at least some of the plurality of capture extenders hybridize to non-contiguous regions of the target nucleic acid. In some embodiments, the detection probe and at least one of the capture extenders hybridize to contiguous (such as adjacent) regions of the target nucleic acid. In some embodiments, where the target nucleic acid has more than one strand, the capture extenders hybridize to the same strand of the target nucleic acid. In some embodiments, where the target nucleic acid has more than one strand, at least some of the capture extenders hybridize to different strands of the target nucleic acid. In some embodiments, step a) is carried out before step b). In some embodiments, step a) is carried out after step b). In some embodiments, step a) and step b) are carried out concurrently. In some embodiments, the sample is a biological sample. In some embodiments, the biological sample is selected from the group consisting of a cell lysate, a tissue homogenate, a blood sample, a plasma sample, a serum sample, a dried blood spot, a blood clot, a nasal swab, a pharyngeal swab, a cheek swab, urine and saliva. In some embodiments the target nucleic acid is free in the biological sample, such as not within a cell. In some embodiments, the target nucleic acid is bound within cells in the biological sample, and the method further comprises lysis of the cells prior to steps a) and b). In some embodiments, the target nucleic acid is RNA. In some embodiments, the RNA is messenger RNA. In some embodiments, the RNA is ribosomal RNA, such as 18S rRNA. In some embodiments, the target nucleic acid is DNA, such as genomic DNA.

The PCR products may also be identified by an enzyme-linked immunosorbent assay (ELISA). The PCR product may be labeled during amplification with an antigen, for example digoxigenin. The labeled PCR product is then captured on a multiwell plate having thereon a nucleic acid probe that hybridizes to the target specific region of the detection probes, which region is present in the amplified product. The labeled captured product may then be detected by adding an enzyme-conjugated antibody against the antigen label, for example horseradish peroxidase anti-digoxigenin antibody, and a color indicator to each well of the multiwell plate. The optical density of each well provides a measure of the amount of PCR product, which in turn indicates the presence of the target nucleic acid in the original sample.

Depending upon the nature of the label, various techniques can be employed for detecting the presence of the label. For fluorescers, a large number of different fluorometers are available. For chemiluminescers, luminometers or films are available. With enzymes, a fluorescent, chemiluminiscent, or colored product can be provided and determined fluorometrically, luminometrically, spectrophotometrically or visually. The various labels which have been employed in immunoassays and the techniques applicable to immunoassays can be employed with the subject assays.

The present methods may be used with routine biological samples obtained for testing purposes by a clinical diagnostic laboratory. In some embodiments, biological samples that may be used in the present methods include, inter alia, whole blood, dried blood spots, separated white blood cells, a plasma sample, a serum sample, cultured cells, tissue biopsies, nasal swabs, pharyngeal swabs, cheek swabs, sputum, urine and the like, i.e., any patient sample normally sent to a clinical laboratory for analysis.

The methods described herein may be useful in a high-throughput setting, i.e., at least about any of 100, 200, 300, 400, 500, 600, 700, 800, 900, 1000, 2000, 3000, 4000, 5000, or 10,000 biological samples may be processed at the same time by carrying out any one of the methods described herein.

In some embodiments, there is provided a sample-pooling strategy for detecting a target nucleic acid in each of a plurality of samples comprising: a) randomly distributing said plurality of samples to be assayed into an n×m matrix (n=m or n=m+1), wherein m is determined by the sample size; b) pooling portions of each sample from each row and pooling portions of each sample from each column; c)

detecting the presence of the target nucleic acid in the pooled samples using any of the methods described herein; and d) re-testing samples at the intersection of a positive row and a positive column individually, wherein samples at the intersection of a negative row and a negative column are declared negative for the target nucleic acid and individually re-tested samples found positive for the target nucleic when re-tested are declared positive for the target nucleic acid.

The present ligation-dependent amplification methods are particularly useful for detection of target sequences in formalin fixed, paraffin embedded (FFPE) specimens, and overcome deficiencies of the prior art method of reverse transcription polymerase chain reaction (RT-PCR) for detection of target RNA sequences in FFPE specimens. RT-PCR has a variable detection sensitivity, presumably because the formation of RNA-RNA and RNA-protein crosslinks during formalin fixation prevents reverse transcriptase from extending the primers. In the present methods the probes can hybridize to the targets despite the crosslinks, reverse transcription is not required, and the probe, rather than the target sequence, is amplified. Thus the sensitivity of the present methods is not compromised by the presence of crosslinks.

A general schematic description of the detection of a target nucleic acid in a biological sample using nucleic acid hybridization-based capture and ligation-enabled PCR is provided in FIG. 1.

Probes and PCR Primers

The polynucleotide probes and PCR primers useful for the methods of the present invention may be synthesized from nucleoside triphosphates by known automated polynucleotide synthetic techniques, e.g., via standard phosphoramidite technology utilizing a nucleic acid synthesizer. Such synthesizers are available, e.g., from Applied Biosystems, Inc. (Foster City, Calif.).

In some embodiments, the methods use polynucleotide probes for the capture and detection of a target nucleic acid as depicted in FIG. 2. In some embodiments, there is provided a plurality of polynucleotide detection probes, e.g., a first detection probe (5' detection probe) and a second detection probe (3' detection probe), and a plurality of polynucleotide capture extenders, e.g., a first capture extender (capture extender 1) and a second capture extender (capture extender 2). In some embodiments, there is further provided an additional detection probe that is an internal detection probe (internal detection probe 1, IDP1). In some embodiments, there is provided a plurality of internal detection probes. In some embodiments there is provided a polynucleotide capture probe. In some embodiments there is provided a plurality of capture probes. The probes may be either deoxyribonucleic or ribonucleic acid molecules, with the choice of molecule type depending on the subsequent amplification method. Reference to "probe" herein generally refers to multiple copies of a probe. Nucleotides with modified backbones are also contemplated.

In some embodiments, the detection probes comprise two probes (5' detection probe and 3' detection probe) that each comprise a sequence complementary to a region of the target nucleic acid (such sequence is referred to herein as CR). In some embodiments, the 5' and 3' detection probes further comprise a sequence that is not complementary to any region of the target nucleic acid (such sequence is referred to herein as NCR). See FIG. 2. In some embodiments, the NCRs of the 5' and 3' detection probes comprise generic 5' and 3' primer binding sites, respectively, and can be combined with distinct CRs that are complementary to different target nucleic acid sequences, allowing for use of a single PCR primer pair for subsequent amplification and detection of distinct ligated detection sequences specific to different target nucleic acid sequences. In some embodiments, the detection probes further comprise at least one internal detection probe (IDP) that is complementary to a region of the target nucleic acid that is flanked by the detection targeting sequences of the 5' and 3' detection probes. In some embodiments, the detection probes targeting a single nucleic acid are designed such that their detection targeting sequences are contiguous, e.g., they are separated by no more than about 500 nucleotides (such as about any of 0, 50, 100, 150, 200, 250, 300, 350, 400, 450 or 500 nucleotides). In some embodiments, the detection probes targeting a single nucleic acid are designed such that their detection targeting sequences are adjacent, i.e., the detection targeting sequences comprise an uninterrupted sequence of the target nucleic acid. In some embodiments, the detection probes targeting a single nucleic acid are designed such that at least some of their detection targeting sequences are non-contiguous, e.g., they are separated by at least about 500 nucleotides (such as about any of 550, 750, 1000, 1500, 2000, 2500, 3000, 3500, 4000, 4500 or 5000 bases). The detection targeting sequences are non-overlapping.

In some embodiments, the 5' ends of the 5' detection probe and any internal detection probes are phosphorylated. In some embodiments, the 5' ends of the 5' detection probe and any internal detection probes are not phosphorylated.

In some embodiments, each of the polynucleotide detection probes is about 20 to about 200 nucleotides in length, for example about 20 to about 40, about 40 to about 60, about 60 to about 80, about 80 to about 100, about 100 to about 120, about 120 to about 140, about 140 to about 160, about 160 to about 180, about 180 to about 200 nucleotides in length. In some embodiments, after ligation of the probes, the ligated detection sequence is at least about 80 to about 400, including for example about 80 to about 120, about 120 to about 160, about 160 to about 200, about 200 to about 300, about 300 to about 400 nucleotides in length. The length of the ligated detection sequence is such that the sequence is suitable for amplification via PCR, LAMP, Qβ replicase or SDA reactions. In some embodiments, the ratio of the length of the CR to the length of the NCR for the 5' and 3' detection probes is about 0.5 to about 2.

In some embodiments, each of the capture extenders comprises a capturing sequence (CS) and an immobilizing sequence (IS), wherein the capturing sequence is complementary to a region of the target nucleic acid and the immobilizing sequence is not complementary to any regions of the target nucleic acid and comprises a sequence that is complementary to a portion of a capture probe, as depicted in FIG. 2. In some embodiments, the immobilizing sequences of the capture extenders are generic, and can be combined with distinct capturing sequences specific for different target nucleic acid sequences, allowing for the use of a single capture probe that can hybridize to each capture extender. In some embodiments, the immobilizing sequence may be directly linked to the capturing sequence or be spaced therefrom by an intermediate non-complementary sequence. In some embodiments, the capture extenders may comprise other non-complementary sequences if desired. These non-complementary sequences should not hinder the hybridization of the capturing or immobilizing sequences to their targets or cause nonspecific hybridization to occur. In some embodiments, the capture extenders targeting a single nucleic acid are designed such that at least some of their capture targeting sequences are contiguous (such as adjacent), e.g., they are separated by no more than about 500 nucleotides (such as about any of 0, 50, 100, 150, 200, 250, 300, 350, 400, 450 or 500 nucleotides). In some embodiments, the capture extenders targeting a single nucleic acid are designed such that at least some of their capture targeting sequences are non-contiguous, e.g., they are separated by at least about 500 nucleotides (such as about any of 550, 750, 1000, 1500, 2000, 2500, 3000, 3500, 4000, 4500 or 5000 bases). The capture targeting sequences are non-overlapping.

In some embodiments, each of the polynucleotide capture extenders are about 50 to about 300 nucleotides in length, for example about 50 to about 70, about 70 to about 90, about 90 to about 110, about 110 to about 130, about 130 to about 150, about 150 to about 200, about 200 to about 300 nucleotides in length. In some embodiments, the ratio of the length of the capturing sequence to the length of the immobilization sequence in the capture extender is about 0.5:1 to about 2:1, including for example about 0.5:1 to about 1:1, about 1:1 to about 1.5:1, about 1.5:1 to about 2:1.

In some embodiments, the capture probes described herein comprise a sequence that is complementary to the immobilizing sequence of a capture extender. In some embodiments, each of the capture extenders comprises a generic immobilizing sequence, and there is provided a single capture probe that comprises a sequence that is complementary to the generic immobilizing sequence. In some embodiments, there is provided a) a plurality of capture extenders, each comprising distinct immobilizing sequences, and b) a plurality of capture probes, each comprising a sequence complementary to one of the distinct immobilizing sequences. In some embodiments, capture probes are bound to a solid support in such a way as to allow subsequent hybridization to corresponding capture extenders. Hybridization of capture probes with capture extenders bound to a target nucleic acid results in association of the target nucleic acid, along with any hybridized detection probes, with the solid support.

Figure 2A:
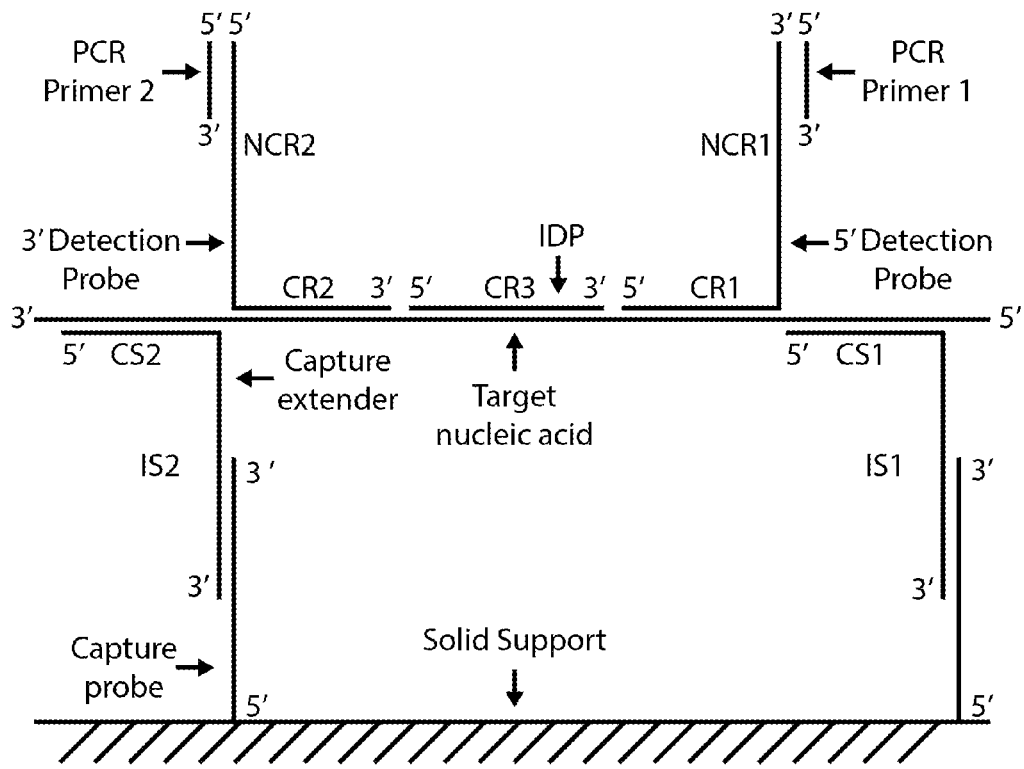
FIGS. 2A and 2B each show a schematic of the structure and features of an exemplary complex formed during capture and detection of a target nucleic acid using nucleic acid hybridization-based capture in combination with ligation-enabled PCR of the present application when using detection probes that ligate to form a linear ligated detection sequence.
Figure 2B:
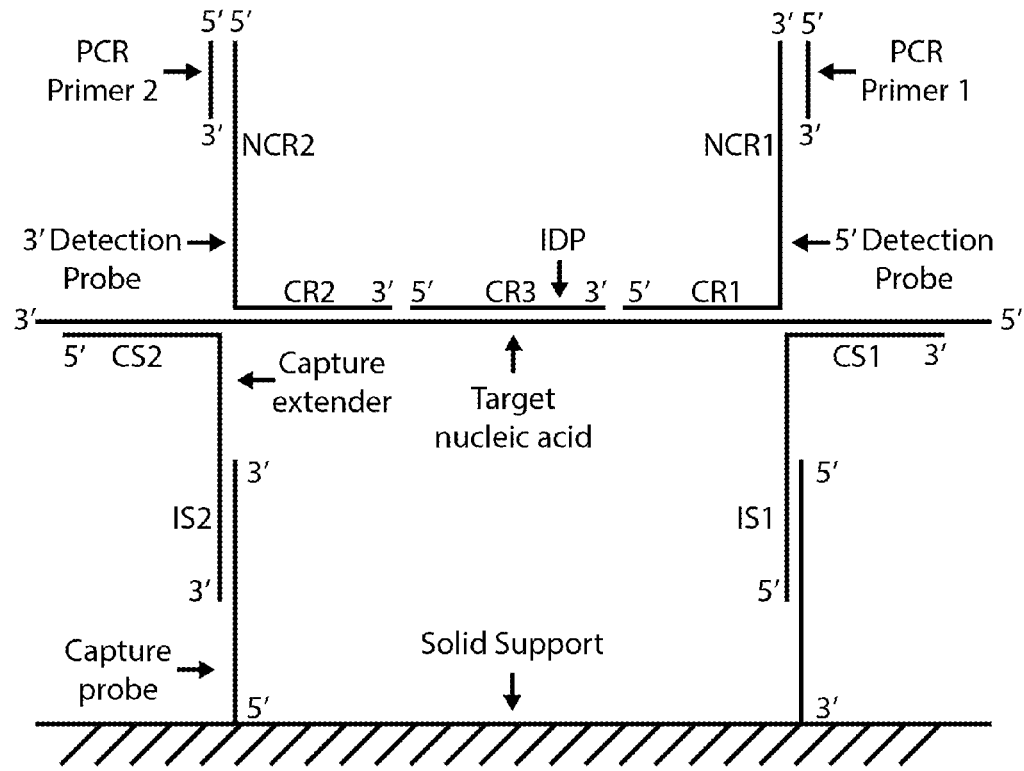

In some embodiments, there are provided: a) capture extenders comprising a 5' capturing sequence and a 3' immobilizing sequence and corresponding capture probes designed to be linked to a solid support at a 5' end, as depicted in FIG. 2A; or b) capture extenders comprising a 3' capturing sequence and a 5' immobilizing sequence and corresponding capture probes designed to be linked to a solid support at a 3' end. In some embodiments, there are provided both a) and b), as depicted in FIG. 2B.

It will be appreciated that hybridization of two nucleic acid sequences need not require perfect complementarity between the sequences. Thus in some embodiments of any of the methods of the present invention, the target-binding sequences of the detection probes and capture extenders need not have perfect complementarity to their target nucleic acid sequences. In some embodiments, the immobilizing sequence of a capture extender need not have perfect complementarity to a sequence in a corresponding capture probe. In some embodiments, heteroduplexes will suffice where fewer than about 20% of the bases (such as fewer than about any of 20, 15, 10 or 5% of the bases) are mismatches, ignoring loops of five or more nucleotides. Thus in some embodiments, detection probes and/or capture extenders comprise fewer than about 20% (such as fewer than about any of 20, 15, 10 or 5%) base pair mismatches with their corresponding target sequence in a target nucleic acid. In some embodiments, capture extenders comprise immobilizing sequences comprising fewer than about 20% (such as fewer than about any of 20, 15, 10 or 5%) base pair mismatches with their target sequence in a corresponding capture probe. In other embodiments, such as when variation-specific detection probes (such as mutation-specific detection probes) are used, homoduplexes with 100% complementarity, i.e., no base pair mismatches, are desirable.

In some embodiments, there is provided a) a plurality of detection probes, such that the detection targeting sequences of detection probes targeting a single nucleic acid are contiguous and non-overlapping, and b) a plurality of capture extenders, such that detection targeting sequences and capture targeting sequences of detection probes and capture extenders targeting a single nucleic are non-overlapping. In some embodiments, there is provided a) a plurality of detection probes, such that the detection targeting sequences of detection probes targeting a single nucleic acid are contiguous and non-overlapping, and b) a plurality of capture extenders, such that detection targeting sequences and capture targeting sequences of detection probes and capture extenders targeting a single nucleic are contiguous and non-overlapping, as depicted in FIG. 2. In some embodiments, the capture targeting sequences are not between detection targeting sequences. The contiguous arrangement of the regions of the target nucleic acid that are complementary to sequences of both the detection probes and the capture extenders allows for increased efficiency of capture of the target nucleic acid complex. This is because 1) interactions between adjacent probes and a target lead to stronger, more stable helix formation due to base-stacking effect between adjacent base-pairings (Dimitrov and Zuker, Biophys. J. 87(1): 215-226, 2004), i.e. due to the base-stacking effect, the hybridization of one capture extender/detection probe with the target will facilitate the hybridization of an adjacent capture extender/detection probe with the target, and the resulting double-helix is more stable than the double-helix formed by hybridization of a single capture extender/detection probe with the target; and 2) hybridization of one capture extender to a capture probe will bring neighboring capture extenders into proximity of nearby capture probes for further hybridization and association with the solid support that the capture probes are bound to, thus increasing the sensitivity of the detection assay. The increased thermodynamic stability of such a configuration will favor binding of target nucleic acid complexes hybridized with multiple capture extenders, thus increasing discrimination over off-target nucleic acids that hybridize with fewer than the full set of capture extenders, leading to increased specificity of the detection assay. This is especially desirable for multiplex PCR reactions where multiple targets within a single reaction may be detected.

In some embodiments of any of the methods of the present invention, the method further comprises providing: a) more than two detection probes; and/or b) more than two capture extenders, increasing the total specific sequences of the detection probes and capture extenders complementary to the target nucleic acid, and thereby affording even higher capture efficiency.

Figure 3A:
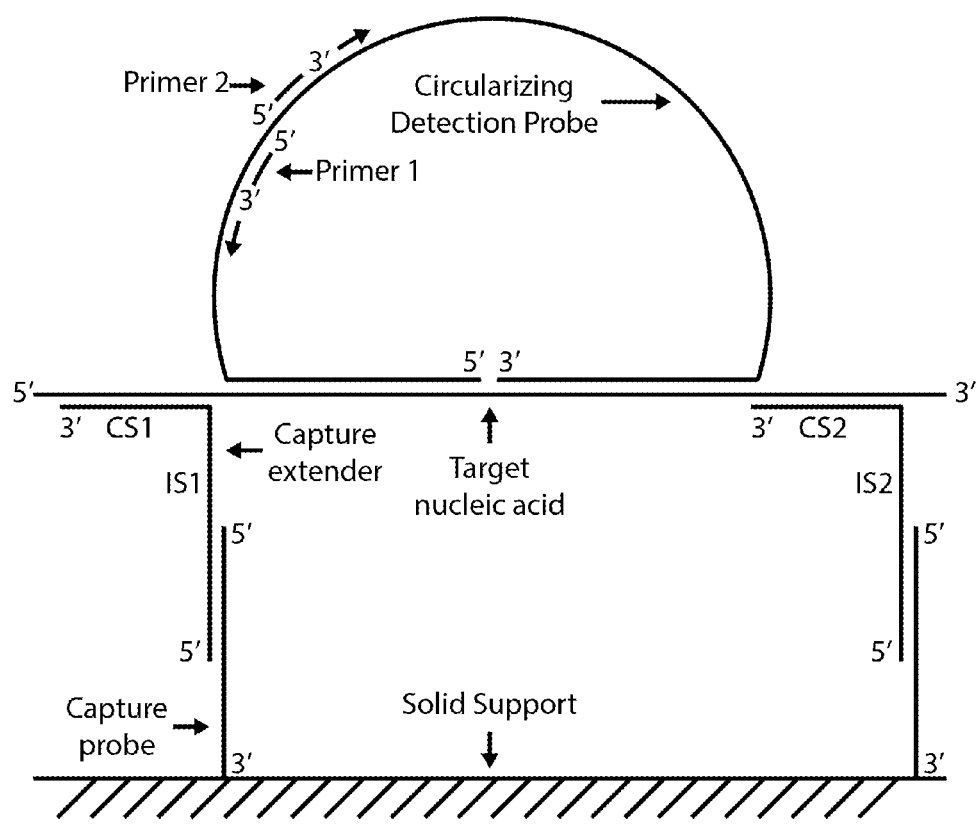
FIGS. 3A and 3B each show a schematic of the structure and features of an exemplary complex formed during capture and detection of a target nucleic acid using nucleic acid hybridization-based capture in combination with ligation-enabled PCR of the present application when using one or more detection probes that ligate to form a circular ligated detection sequence.

A still further aspect of the present invention provides one or more capture extenders, such as those described above, and a single detection probe, also referred to as a circularizing detection probe, that hybridizes to the target nucleic acid and circularizes upon ligation of its free termini, as shown in FIG. 3A. In some embodiments, the circularizing detection probe is designed so that regions of the probe that are complementary to target nucleic acid sequences are located at each end of the probe. In some embodiments, when the circularizing detection probe hybridizes with the target, its termini are placed adjacent to each other, resulting in the formation of a closed circular molecule upon ligation with a linking agent such as a ligase enzyme. This circular molecule, also referred to as a ligated detection sequence, or more specifically a circularized ligated detection sequence, may then serve as a template during an amplification step, e.g. PCR, RCA.

Figure 3B:
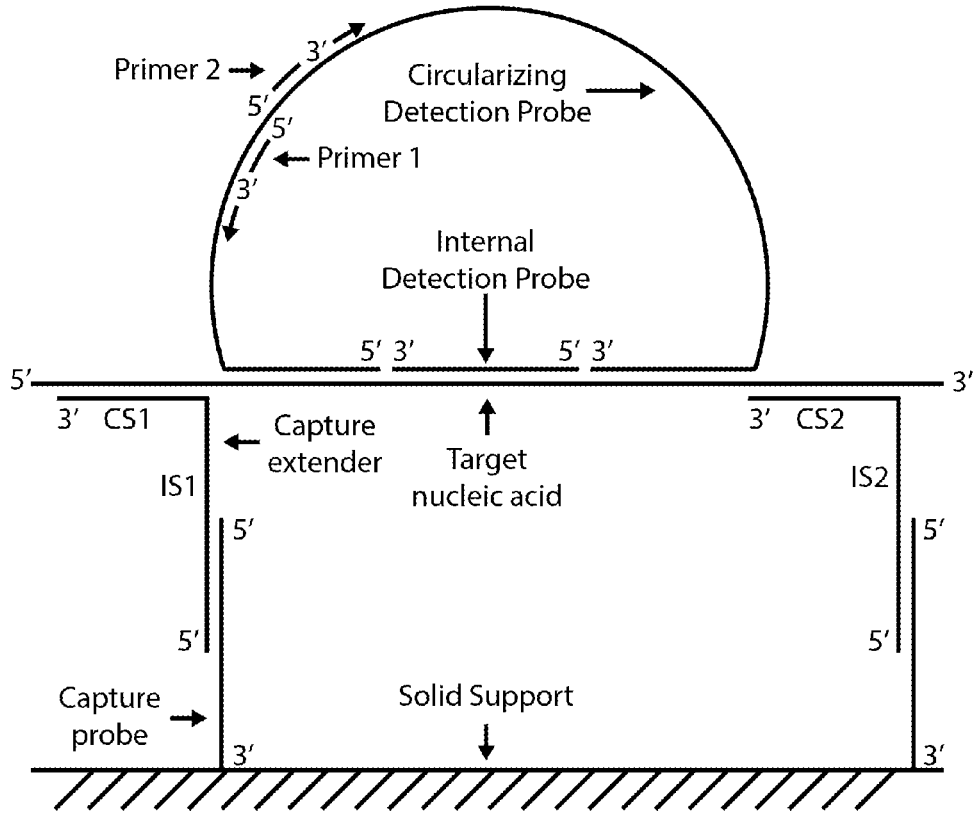

It is further contemplated to use multiple detection probes which can be ligated to form a single covalently closed ligated detection sequence. In some embodiments of any of the methods presented herein, the plurality of detection probes (referred to herein as circularizing detection probes) comprise: a) one or more internal detection probes that hybridize to regions of the target nucleic acid; and b) an additional detection probe comprising i) a 3' terminus that is complementary to a region of the target nucleic acid that is downstream of the regions of the target nucleic acid complementary to the internal detection probes; and ii) a 5' terminus that is complementary to a region of the target nucleic acid that is upstream of the regions of the target nucleic acid complementary to the internal detection probes, which through a plurality of ligation events can form a single covalently closed ligated detection sequence, as depicted in FIG. 3B. In some embodiments, two ligases, e.g. an enzymatic and a chemical ligase, are used to covalently close the circularizing detection probes, wherein the order of the ligations is controlled.

Thus, in some embodiments of any of the methods presented herein, the methods further comprise designing the detection probes to be circularizing detection probes.

Another embodiment of the present invention provides a method of reducing carryover contamination and background in amplification methods utilizing circularizing detection probes. The present ligation-enabled amplification methods, unlike conventional amplification methods, involve amplification of the ligated detection sequence rather than the target nucleic acid. When the ligated detection sequence is a closed circular molecule, it has no free ends susceptible to exonuclease digestion. After circularizing detection probe ligation, i.e. circularization, treatment of the reaction mixture with an exonuclease provides a "cleanup" step and thus reduces background and carryover contamination by digesting unligated detection probes and other linear DNA fragments, but not closed circular molecules. The circularized detection sequences remain intact for subsequent amplification and detection. In conventional PCR, the use of exonuclease to eliminate single stranded primers or carryover DNA fragments poses the risk that target nucleic acid will also be degraded. The present invention does not suffer this risk because target nucleic acid is not amplified. In a preferred embodiment, the exonuclease is exonuclease III, exonuclease VII, mung bean nuclease or nuclease BAL-31. Exonuclease is added to the reaction after ligation and prior to amplification, and incubated, for example at 37° C. for thirty minutes.

Thus, in some embodiments of any of the methods presented herein, the methods further comprise: a) designing the detection probes to be circularizing detection probes; and b) following ligation of the circularizing detection probes, but before amplification of the ligated detection sequence, digesting unligated circularizing detection probes and other linear nucleic acids by exonuclease treatment using any method known in the art.

In some embodiments, a circularized ligated detection sequence can also be amplified and detected by the generation of a large polymer. In some embodiments, the polymer is generated through a) the rolling circle extension of a first primer along the circularized ligated detection sequence and displacement of downstream sequence, producing a single-stranded DNA comprising multiple units of the ligated detection sequence, wherein each unit serves as a template for subsequent amplification; and b) binding and extension of a second primer to the single stranded DNA polymer. By using both primer-extension/displacement and PCR, more detectable product is produced with the same number of cycles.

In some embodiments, the sequences of the detection probes and capture extenders that are complementary to the target nucleic acid are each about 15 to about 60 nucleotides in length, preferably about 18 to about 35 nucleotides in length, which provides a sufficient length for adequate hybridization of the probes to the target nucleic acid. They are designed to hybridize to different sequences of the target nucleic acid. The sequences may be selected based on a variety of considerations. In some embodiments, depending upon the nature of the target nucleic acid, the sequences of the detection probes and capture extenders that are complementary to the target nucleic acid comprise a sequence selected from the group consisting of a consensus sequence, a sequence associated with polymorphisms, a sequence specific to a particular phenotype or genotype, a sequence specific to a particular strain, and the like.

In some embodiments, the primer binding sites of the ligated detection sequence comprise a G-C rich sequence which, upon hybridization to a primer, as discussed below, provides a more stable duplex molecule, i.e., one which requires a higher temperature to denature. In some embodiments, ligated detection sequences comprising G-C rich primer binding sites may be amplified using a two temperature PCR reaction, wherein primer hybridization and extension may both be carried out at a temperature of about 60 to about 65° C. (as opposed to hybridizing at a lower temperature normally used for PCR amplification) and denaturation at a temperature of about 92° C., as discussed below. The use of a two temperature reaction reduces the length of each PCR amplification cycle and results in a shorter assay time.

In some embodiments, the ratio of detection probe and capture extender to anticipated moles of target nucleic acid will each be at least stoichiometric and preferably in excess. In some embodiments, it will be in the range of about 2:1 to about 10,000:1. In some embodiments, concentrations of each of the probes can range from about $10^{-9}$ to about $10^{-6}$ M, with target nucleic acid concentrations varying from about $10^{-18}$ to about $10^{-10}$ M.

PCR primers for use in the present method may be synthesized from nucleoside triphosphates by known automated synthetic techniques, as discussed above for synthesis of the polynucleotide probes. In some embodiments, the PCR primers may be about 10 to about 60 nucleotides in length, preferably about 18 to about 35 nucleotides in length, with lengths of about 16 to about 21 nucleotides being most preferred. It is also preferred that the primers are designed so that they do not have any secondary structure, i.e., each primer contains no complementary region within itself that could lead to self-annealing.

In some embodiments, the high G-C content of the PCR primers and the PCR primer binding sites of the ligated detection sequence permits performing the PCR reaction at two temperatures, rather than the usual three temperature method.

PCR and RT-PCR Reactions

In some embodiments, the PCR and RT-PCR reaction mixtures described herein may comprise dNTPs, primers, thermostable DNA polymerase, and/or buffer.

In some embodiments, DNA polymerases that may be used include, but are not limited to, Taq, Pfu, Vent, and Sequitherm DNA Polymerase (EPICENTRE).

In some embodiments, the PCR and RT-PCR reaction mixtures may be obtained from commercially available kits, for example, a PCT kit, a real-time PCR kit, the One-Step RT-PCR kit or the One-Step RT-qPCR kits.

In some embodiments, suitable buffers may be used to maintain the pH of a PCR reaction, e.g., a zwitterionic buffering agent can be used such as Tricine, HEPES, and Bicine or a non-zwitterionic buffering agent such as Tris can be used. In some embodiments, the buffer can be optimized by including various salts and additives, including magnesium chloride, potassium chloride, ammonium sulfate, gelatin, bovine serum albumin (BSA), dimethylsulfoxide (DMSO), polyamine, betaine, tetramethylammonium chloride (TMAC), and dithiolthreitol (DTT). In some embodiments, non-reducing carbohydrates such as trehalose, sucrose and raffinose and zwitterionic surfactants such as CHAPS can also be used.

A primer pair for use in any of the methods of the present invention can be designed based on the non-complementary regions (NCRs) of the detection probes. In some embodiments, the primer pair will be a generic primer pair, corresponding to generic primer binding sites present in a plurality of ligated detection sequences formed as a result of ligation of detection probes hybridized to their target nucleic acid. In some embodiments, the primers are labeled, for example with a fluorescent dye, for easy detection.

The ligated detection sequence amplified by PCR can be detected by any method known in the art, which can include, for example, real time PCR, fluorescence detection, gel electrophoresis, sequencing, MALDI-TOF mass spectrometry such as the MassARRAY assay, microarray hybridization assay or other methods that perform similar functions.

In some embodiments, real time PCR reactions may be detected with double-stranded DNA-binding dyes, e.g., SYBR Green or EvaGreen. In some embodiments, the Real Time PCR product is detected by incorporating into the primers a fluorescent label, e.g., Cy3, Cy5, Fluorescein, Rhodamine, Rhodamine Red, TET, or other fluorescent molecules.

In some embodiments, a dual-labeled probe which contains a 5' fluorescent reporter and a 3' quencher is used to increase the sensitivity of real time PCR reactions. In some embodiments, the fluorescent reporter is Cy3, Cy5, Fluorescein, Rhodamine, Rhodamine Red, TET or other fluorescent molecules. In some embodiments, quenchers that are used include BHQ-1, TAMRA, BHA-2, BHQ-3 and other quenching molecules. In some embodiments, a dual-labeled probe that contains a 5' fluorescent reporter and a 3' quencher and forms a hairpin structure is used to increase the sensitivity of the real time PCR.

In some embodiments of any of the methods of the present invention, the amplification and detection of a ligated detection sequence comprises: a) using RT-qPCR to amplify the ligated detection sequence, wherein a Ct value is determined; and b) comparing the determined Ct value to a predetermined threshold Ct, wherein a Ct value below the predetermined threshold is indicative of the presence of the ligated detection sequence in the sample. In some embodiments, the threshold Ct is set to 40. In some embodiments, the threshold Ct is about any of 35, 36, 37, 38, 39 or 40. In some embodiment the threshold Ct is set experimentally as the Ct of a control reaction, wherein all reaction conditions, including reagent concentration and cycling temperatures, are identical to test reactions except that the target nucleic acid is known to be absent.

Variations on PCR have been developed and can be used with the present invention. In some embodiments, the PCR reaction is nested using two sets of primers and two successive PCR runs to increase specificity. Alternatively, in some embodiments the PCR reaction is multiplexed by adding multiple sets of primers to the reaction.

In some embodiments, annealing of the primers to the ligated detection sequence is carried out at about 37 to about 50° C.; extension of the primer sequence by Taq polymerase in the presence of nucleoside triphosphates is carried out at about 70 to about 75° C.; and the denaturing step to release the extended primer is carried out at about 90 to about 95° C. In some embodiments, a two temperature PCR technique is used, and the annealing and extension steps are both carried out at about 60 to about 65° C., thus reducing the length of each amplification cycle and resulting in a shorter assay time.

For example, a suitable three temperature PCR amplification (as provided in Saiki et al., Science 239:487-491, 1988) may be carried out as follows:

Polymerase chain reactions (PCR) are carried out in about 25-50 µl samples containing 0.01 to 1.0 ng of template ligated detection sequence, 10 to 100 pmol of each generic primer, 1.5 units of Taq DNA polymerase (Promega Corp.), 0.2 mM dATP, 0.2 mM dCTP, 0.2 mM dGTP, 0.2 mM dTTP, 15 mM MgCl2, 10 mM Tris-HCl (pH 9.0), 50 mM KCl, 1 µg/ml gelatin, and 10 µl/ml Triton X-100 (Saiki, 1988). Reactions are incubated at 94° C. for 1 minute, about 37 to about 55° C. for 2 minutes (depending on the identity of the primers), and about 72° C. for 3 minutes and repeated for 30-40, preferably 35, cycles. A 4 µl-aliquot of each reaction is analyzed by electrophoresis through a 2% agarose gel and the DNA products in the sample are visualized by staining the gel with ethidium-bromide.

The two temperature PCR technique, as discussed above, differs from the above only in carrying out the annealing/extension steps at a single temperature, e.g., about 60 to about 65° C. for about 5 minutes, rather than at two temperatures. For example, a ligated detection sequence can be detected by real-time quantitative PCR by adding 25 ul of a PCR mixture containing 1×SYBR® Premix Ex (Takara, RR820) and 100 nM primers to each well of a micro-well plate containing ligated detection sequence prepared as described in any of the methods of the present invention, amplifying and detecting on a Roche LC480 II using an initial denaturing step of 30 sec at 95° C. followed by 45 cycles with 5 sec denaturing at 95° C. and 20 sec annealing at 60° C.

Pathogens to be Detected

The methods described herein can be used for diagnosing diseases, for example diseases associated with any one of the pathogens described herein. In some embodiments, the individual has no symptom of the disease.

Examples of diseases that can be diagnosed include, but are not limited to: malaria, for example by detecting protozoans of the genus *Plasmodium*; hepatitis, for example by detecting the hepatitis A, B or C virus; HIV infections, for example by detecting the human immunodeficiency virus; herpes, for example by detecting herpes simplex virus type 1 or herpes simplex virus type 2; mononucleosis, for example by detecting the Epstein-Barr virus; sleeping sickness, for example by detecting trypanosomes; chickenpox, for example by detected by the varicella zoster virus, measles and mumps by detecting the Paramyoxviridae family viruses, staph infections or toxic shock syndrome by detecting *Staphylococcus aureus*, gas gangrene by detecting *Clostridium perfringens*, conjunctivitis by detecting *Haemophilus aegyptius*, whopping cough by detecting *Bordetella pertussis*, tuberculosis by detecting *Mycobacterium tuberculosis*, Legionnaires disease by detecting *Legionella pneumophilia*, anthrax infections by detecting *Bacillus anthracis*, syphilis by detecting *Treponema pallidum*, cholera by detecting *Vibrio cholerae*, typhoid fever by detecting *S. Typhi*, peptic ulcer disease by detecting *Heliobacter pylori*, tetanus by detecting *Clostridium tetani*, botulism by detecting *Clostridium botulinum*, lyme disease detected by *Borrelia burgdorferi*, *B. Garinii*, and *B. afzelii*, and influenza by detecting the H5N1, H1N1, H3N2, H7N9 and other viruses.

Pathogens that can be detected using the methods described herein include, but are not limited to, bacterium, fungus, viruses, archaea, protists, protozoa and spores. In some embodiments, the pathogen is thermal stable.

In some embodiments, the pathogen is a protozoan. Exemplary protozoa include, but are not limited to, *Plasmodium falciparum, Plasmodium vivax, Plasmodium ovale, Plasmodium malariae, Plasmodium knowlesi, Leishmania tropica, Trypanosoma brucei, Trypanosoma cruzi, Cryptosporidium, Entamoeba histolytica, Giardia lamblia*, and *Toxoplasma gondii*.

In some embodiments, the pathogen is a virus. Exemplary viruses include, but are not limited to, HIV-I, HIV-2, hepatitis viruses (including hepatitis B and C), Ebola virus, West Nile virus, and herpes virus such as HSV-2, adenovirus, dengue serotypes 1 to 4, ebola, enterovirus, herpes simplex virus 1 or 2, influenza, Japanese equine encephalitis, Norwalk, papilloma virus, parvovirus B19, rubella, rubeola, vaccinia, varicella, Cytomegalovirus, Epstein-Ban virus, Human herpes virus 6, Human herpes virus 7, Human herpes virus 8, Variola virus, Vesicular stomatitis virus, Influenza virus B, Measles virus, Polyomavirus, Human Papilomavirus, Respiratory syncytial virus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Human T-cell Leukemia virus type-1, Hanta virus, Rubella virus, Simian Immunodeficiency viruses, H3N2 virus, H5N1 virus, H1N1 virus and any combination thereof.

In some embodiments, the pathogen is an influenza virus. Influenza virus can be divided into three groups: influenza A, influenza B, and influenza C. Influenza type A and B viruses cause seasonal epidemics. Type A influenza viruses are characterized according to their hemagglutinin (HA) type and their neuraminidase (NA) types. There are 17 different H antigens (H1 to H17) and 10 different N antigens (N1 to N10) for a total of 170 different possible combinations. Furthermore, there are strains within each type containing genetic variation. In every epidemic season, different influenza variants circulate in the human population which can lead to gene exchange and may lead to new and more pathogenic variants. Therefore it is of vital importance to monitor and be able to detect and diagnose types and subtypes of influenza viruses.

Influenza A viruses can infect humans, birds, swine, horses, dogs, whales, seals, and cats. Birds are asymptomatic carriers of influenza A viruses. Furthermore, some strains of influenza A viruses can be transmitted between different species, for example from pigs or birds to humans. Therefore it is contemplated that the present method of detection of pathogens can be used to detect influenza infections in humans as well as animals.

The H1N1 virus is a type of influenza A virus. H1N1 is a major cause of seasonal influenza, which affects approximately 15 percent of the global population annually. Additionally, the H1N1 virus has caused several major epidemics and pandemics. For example, the influenza pandemic of 1918-19 was the most destructive influenza outbreak has been estimated to have killed 25 million people and was caused by the H1N1 virus. In 2009, another H1N1 outbreak occurred, originating in swine and spread throughout the world causing a pandemic.

H7N9 and H5N1 are also influenza type A avian influenza viruses. The H7N9 virus was first reported in China in April of 2013 and has been reported in birds and humans. Despite numerous cases of H7N9 virus infection associated with poultry exposure, there has been no evidence of sustained onwards virus transmission to other people. Whereas previous infections with subtype H7 avian influenza viruses were mild, the new H7N9 strain has resulted in over 40 fatalities. Clinical findings in patients with confirmed H7N9 infections include high fever, non-productive and product cough, shortness of breath, dyspnea, hypoxia, evidence of lower respiratory tract disease with opacities, consolidation and infiltrates noted on chest imaging. Complications of the H7N9 virus include septic shock, respiratory failure, acute respiratory distress syndrome, refractory hypoxemia, acute renal dysfunction, multiple organ dysfunction, rhabdomyolysis, encephalopathy, and bacterial and fungal infections.

Influenza viruses can be detected by probes targeting the HA or NA genes. The probes can be designed to amplify a specific type. For example H1 universal probes can be used to detect H1 viruses of avian, swine, and human origin. Alternatively, probes can be designed to specifically detect subtypes of the virus. For example, a probe targeting H1N1 of human origin can be designed that will not target the H1N1 virus of swine origin. As another example, the HA gene fragments between nucleotides 125 and 302 can be used and probes that can differentiate between the pandemic and seasonal H1N1 strains can be designed. Similar methods can be employed to detect other influenza strains and subtypes.

In some embodiments, the pathogen is a fungus or a yeast. Exemplary fungi and yeast include, but are not limited to, *Cryptococcus neoformans, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Aspergillus fumigatus, Aspergillus flavor, Aspergillus clavatus, Cryptococcus neoformans, Cryptococcus laurentii, Cryptococcus albidus, Cryptococcus gattii, Histoplasma capsulatum, Pneumocystis jirovecii, Pneumocystis carini, Stachybotrys chartarum*, and any combination thereof.

In some embodiments, the pathogen is a bacterium. Exemplary bacteria include, but are not limited to: anthrax, *Campylobacter*, cholera, diphtheria, enterotoxigenic *E. coli, giardia*, gonococcus, *Helicobacter pylori*, Hemophilus influenza B, Hemophilus influenza non-typable, meningococcus, pertussis, pneumococcus, *salmonella, shigella, Streptococcus* B, group A *Streptococcus*, tetanus, *Vibrio cholerae, yersinia, Staphylococcus, Pseudomonas* species, Clostridia species, Myocobacterium tuberculosis, *Mycobacterium leprae, Listeria monocytogenes, Salmonella typhi, Shigella dysenteriae, Yersinia pestis, Brucella* species, *Legionella pneumophila*, Rickettsiae, *Clostridium perfringens, Clostridium botulinum, Staphylococcus aureus*,

*Treponema pallidum, Haemophilus influenzae, Treponema pallidum, Klebsiella pneumoniae, Pseudomonas aeruginosa, Cryptosporidium parvum, Streptococcus pneumoniae, Bordetella pertussis, Neisseria meningitides*, and any combination thereof.

In some embodiments, the pathogen is a plant pathogen. Exemplary plant pathogens include, but are not limited to, e.g., *Aspergillus niger, Aspergillus aculeatus, Botrytis cinerea, Cladosporium cladosporioides, Penicillium* spp., *Saccharomyces cerevisiae*, plum pox virus, *Phomopsis viticola, Erwinia amylovora, chrysanthemum* clorotic mottle viroid, *chrysanthemum* stunt viroid, potato spindle tuber viroid, hop latent viroid, avocado sunblotch viroid, tomato chlorotic viroid, citrus exocortis voroid, coconut cadang-cadang viroid, coconut tinangaja viroid, tomato plant macho viroid, *Candidatus Liberibacter asiaticus, Cordana johnstonii, Fusarium, oxysporum, Albugo candida, Claviceps purpurea, Puccinia coronata, Guignardia citricarpa, Hemileia coffeicola, Hemileia vastatrix, Ashbya gossypii, Phymatotrichopsis omnivora, Anguina* spp., *Antrodia* spp., *Armillaria* spp., *Botryodiplodia* spp., *Botryosphaeria* spp., *Cercospora* spp., *Cochliobolus* spp., *Diaphorthe* spp., *Fusarium* spp., *Heterodera* spp., *Leptosphaeria* spp., *Mycosphaerella* spp., *Oidium* spp., *Peronospora* spp., *Pestalotiosis* spp., *Phoma* spp., *Phytophthora* spp., *Pseudocercospora* spp., *Phythium* spp., *Ramularia* spp., *Septoria* spp., *Taphrina* spp., *Uromyces* spp., *Venturia* spp., and *Xanthomonas* spp.

In some embodiments, the pathogen is a food pathogen. Exemplary food pathogens include, but are not limited to, e.g., *Bacillus cereus, Campylobacter jejuni, Clostridium botulinum, Clostridium perfringens, Cryptosporidium parvum, Escherichia coli* 0157:H7, *Giardia lamblia*, Hepatitis A, Hepatitis E, *Listeria monocytogenes, Shigella flexneri*, Norwalk or Norwalk-like virus, norovirus, *Salmonella* spp., *Staphylococcus* spp., *Toxoplasma gondii, Vibrio* spp., *Yersinia* spp., caliciviruses, Sapporo virus, rotavirus, astrovirus, ergot fungus, *Aspergillus flavus, Aspergillus parasiticus, Claviceps* spp., *Trichinella*, Avian influenza, *Streptococcus* spp., *Brucella* spp., *Corynebacterium ulcerans, Coxiella burnetii, Pleisomonas shigelloides, Aeromonas sobira, Aeromonas hydrophilia, Aeromonas caviae*, and others.

Kits and Devices

Also provided herein are kits useful for carrying out any one of the methods described herein. For example, in some embodiments, there is provided a kit comprising: 1) a plurality of capture extenders, 2) a plurality of detection probes; and 3) a plurality of capture probes. In some embodiments, the kit further comprises a solid support. In some embodiments, the capture probes are immobilized on the solid support. In some embodiments, the kit further comprises one or more sets of primers for PCR amplification.

The kit may further comprise, for example, a reaction mixture for carrying out the lysis and hybridization steps of the present invention. In some embodiments, the kit comprises a lysis mixture, such as, for example, a solution comprising about 10 to about 20 mM Tris-HCl (such as about 15 mM Tris-HCl), about 130 to about 170 mM NaCl (such as about 150 mM NaCl), about 0.5 to about 2 mM EDTA (such as about 1 mM EDTA), and about 0.5 to about 2% Triton X-100 (such as about 1% Triton X-100). In some embodiments, the lysis solution further comprises about 0.5 to about 2 mM EGTA (such as about 1 mM EGTA). In some embodiments, the lysis solution further comprises about 0.5 to about 3 mg/ml proteinase K (such as about 1.5 mg/ml proteinase K). In some embodiments, the lysis solution further comprises a probe mix that comprises detection probes and capture extenders.

In some embodiments, the detection probes and capture extenders target a single target nucleic acid. In some embodiments, the detection probes and capture extenders target a plurality of different target nucleic acids. In some embodiments, the kit comprises capture probe that can be conjugated to a solid support. In some embodiments, the kit comprises capture probe conjugated to a solid support, such as the surface of wells in a 96-well plate. In some embodiments, the kit comprises beads that can be conjugated with the capture probe. In some embodiments, the kit comprises beads that are pre-conjugated with the capture probe. In some embodiments, the kit further comprises an instruction for carrying out any one of the methods described herein. In some embodiments, the kit further comprises a positive or negative control sample. In some embodiments, the kit further comprises a control set of detection probes and capture extenders for a control nucleic acid in the biological sample.

EXAMPLES

The following examples are offered to illustrate but not to limit the invention.

Example 1: Sensitive, Low Cost Active Molecular Screening for Malaria Parasites in Pooled Dried Blood Spots from Local Resident and Returned Travelers in China Materials and Methods
Field Samples from Study Cohort Blood smears and dried blood spots were collected from two cohorts from May to October, 2013. The first (n=505) was from Qiushan, Yunnan, China, including 226 local residents and 279 primary school children. While two children had been diagnosed with *Plasmodium vivax* infection in the past 6 months, none of the people tested in this study showed malaria-related symptoms at sampling day. Whole blood samples of this cohort were collected in EDTA or heparin tube and stored at −20° C. until real time PCR test. The second cohort (n=2855) was from Tengchong, Yunnan and Feidong, Anhui, China, consisting of local patients and travelers (n=560) returning from malaria-endemic settings.

Samples were collected with written informed consent. Ethical approval was granted by the Institutional Review Board (IRB) of the Institute of Basic Medical Sciences, Chinese Academy of Medical Sciences.

Detection of 18S rRNA by Ligation-Enabled PCR 3 mm diameter punched-out circles of DBSs were lysed with 100 µl of Lysis Mixture (Diacurate Inc, Beijing, China), 191 µl of water, 3 µl probe mix of detection probe 1 (SEQ ID NO: 1), detection probe 2 (SEQ ID NO: 2), internal detection probe (SEQ ID NO: 3), capture extender 1 (comprising capturing sequence 1, SEQ ID NO: 4, operably linked to a sequence complementary to 17 bases of the capture probe), capture extender 2 (comprising capturing sequence 2, SEQ ID NO: 5, operably linked to a sequence complementary to 17 bases of the capture probe) and capture extender 3 (comprising capturing sequence 3, SEQ ID NO: 6, operably linked to a sequence complementary to 17 bases of the capture probe), each specific for *Plasmodium* sp. 18S rRNA, and 3 µl proteinase K (50 mg/ml) at 56° C. for 30 min with vigorous shaking (pooled blood spots were lysed as a single punch). The lysates were then transferred to a 96-well plate pre-conjugated with capture probe (Malaria PAN HT- PCR Screening 1.0 kit, Diacurate Inc, Beijing, China). After overnight incubation at 55° C., each well was washed 3 times with 150 μl wash buffer (Diacurate Inc, Beijing, China), and then incubated with 50 μl ligation buffer (Diacurate Inc, Beijing, China) at 37° C. for 30 minutes. The plate was then washed again similarly, and used for real time qPCR with 25 μl/well of PCR mixture containing 1×SYBR® Premix Ex (Takara, RR820) and 100 nM primers (PCR primer 1, SEQ ID NO: 7 and PCR primer 2, SEQ ID NO: 8). Amplification and detection were performed on Roche LC480II under the following conditions: 30 s at 95° C., and 45 cycles of 5 s at 95° C. and 20 s at 60° C. The melt curve was prepared from 65° C. to 90° C. using default settings. A sample was considered positive if Ct<40 and the melting curve was the same as in the positive control. At least one positive control and one negative control were included in each experiment. Each test was performed in duplicate.

Diagnosis by RDT

RDT tests of each sample in this study were done with CARESTART™ (Accessbio, Monmouth Junction, N.J.) according to the manufacturer's protocol. The kit is among the list of RDT procurement recommendations issued by W.H.O. (W.H.O., Information note on recommended selection criteria for malaria rapid diagnostic tests (RDTs), http://www.who.int/malaria/diagnosis_treatment/diagnosis/RDT_selection_criteria.pdf).

Diagnosis by Standard Real Time qPCR

DNA was extracted from 200 μl of thawed blood or dried blood spots with QIAamp DNA Blood Mini Kit (QIAGEN), according to the manufacturer's instructions. The genus Plasmodium 18s rRNA screening primers, probe sequences and real-time qPCR conditions were adopted from Rougemont et al (Rougemont et al., J. Clin. Microbiol. 42(12): 5636-43, 2004). If the Ct was greater than 40 the sample was considered negative. At least one positive and one negative sample were included for each experiment. Each sample was tested in duplicate.

Pool Size

To determine the ability of ligation-enabled PCR to detect target RNA in pooled dried blood spots, we prepared controls by spotting 75 μl cultured Plasmodium falciparum strain 3D7 (50 parasites/μl), or whole blood from healthy volunteers, to Whatman 3MM filter paper, and air dried for 4 hours. Punches 3 mm in diameter were removed from the positive control Plasmodium falciparum spot and the negative control dried blood spots, and 1 positive control punch was combined with 0, 10, 20, 25 or 35 negative control punches. The pooled punches were lysed using a standard lysis protocol and tested in duplicate using ligation-enabled PCR.

Pooling Strategy Applied to Active Screening

We adopted a matrix pooling strategy. All samples were distributed randomly in an n×m matrix (n=m or n=m+1, m determined by sample size), samples were pooled according to row and column, and the pools were tested by ligation-enabled PCR. In this way, each sample was tested once in a row pool and once in a column pool. Samples at the intersection of positive row and column pools were tested again individually, and all others were declared negative. Each test was run in duplicate.

Results

Analytical Performance of Ligation-Enabled PCR

Figure 4:
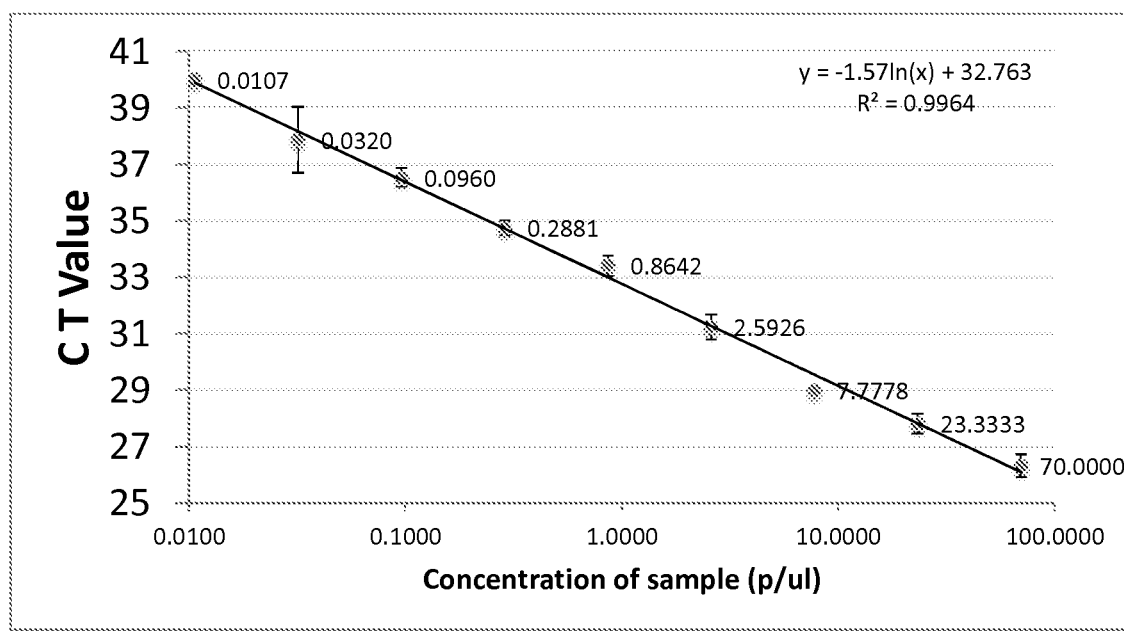
FIG. 4 shows the quantitative nature of the LE-PCR technique, where Ct values from RT-qPCR of a sample correlate with the concentration of *Plasmodium falciparum* in the sample.

We first made a 3-fold, 11-point serial dilution of fresh human erythrocyte-cultured Plasmodium falciparum (isolate 3D7), ranging from 70 p/μl to 0.0012 p/μl. The limit of detection was determined as the minimal amount of erythrocyte-cultured Plasmodium falciparum added to the healthy human blood that yields a positive result. The assay gave a detection limit of about 0.01 parasites/μl, with signals proportional to parasite numbers ($R^2$=0.996) (FIG. 4, standard curve), indicating that our assay is highly sensitive, and able to quantify low parasitemia in intact samples. Whole blood samples collected from healthy volunteers were used as negative control.

Figure 5:
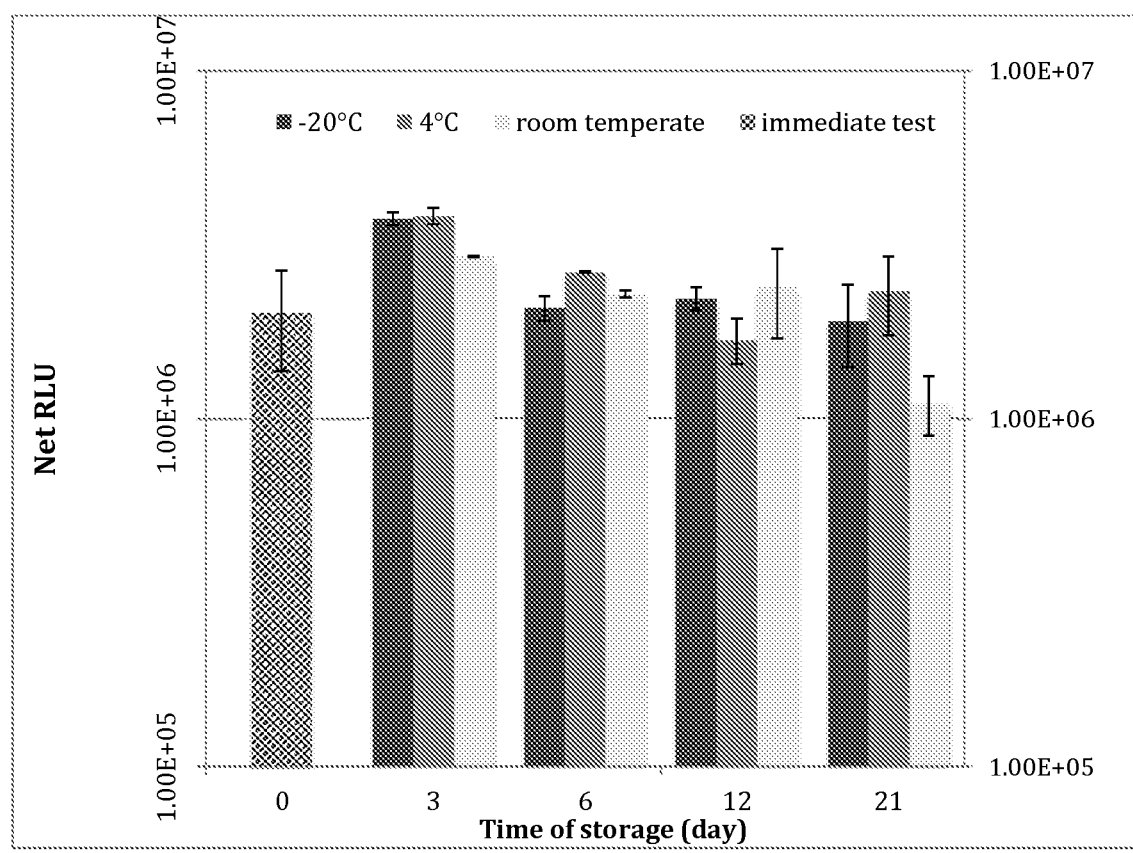
FIG. 5 shows the stability of 18S rRNA from dried blood spots stored at various temperatures, as assayed by RNA hybridization using branched DNA probes for detection.

Stability of Plasmodium 18S rRNA in Dried Blood Spots Stored at Different Temperature We simulated collection of dried blood spots in the field by spotting cultured Plasmodium falciparum (50 p/μl) in 75-μl aliquots onto Whatman 903 filter paper, air drying for 4 hours, sealing in a plastic bag with desiccant, and storing at either room temperature, 4° C. or −20° C. until use. At day 3, 6, 12 and 21, one 3 mm diameter punch was removed from each of the differently stored dried blood spots and subject to cell lysis. Lysates were stored at −20° C. prior to testing. Our previous study indicated that RNA in such a lysate is stable at −20° C. for more than 3 month (Cheng et al., J. Clin. Microbiol. 51(1): 125-30, 2013). All lysates were tested in parallel at day 21 by RNA hybridization assay. No significant 18S rRNA degradation was observed (FIG. 5, storage and signal).

Pool Size

Figure 6:
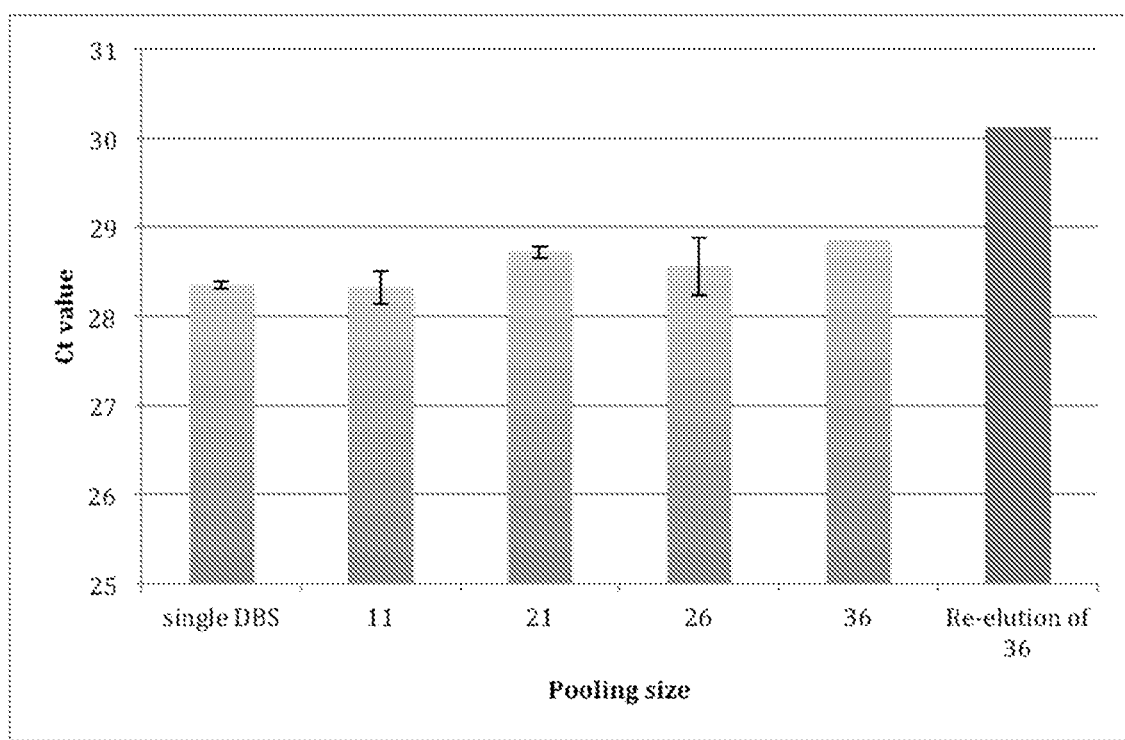
FIG. 6 shows the retention of detection sensitivity of LE-PCR with pooled samples derived from dried blood spots.

Although pooling of positive DBSs with negative ones did not significantly reduce detection signal (FIG. 6, pool size), pooling of more than 20 punches made it difficult to pipette enough lysate for performing duplicate tests. A second elution of large pools gave only reduced signal (FIG. 6, pool size). Although centrifugation can be used to retrieve lysate more effectively, this would add complexity to the test and potentially give rise to cross-contamination. A pool size of smaller than 20 is therefore identified as an optimal strategy. For the active malaria screening carried out in the present study, where DBS samples arrived in our laboratory in batches, to provide timely diagnostic results samples were tested once a sufficient number were received to allow for a matrix pooling strategy with a pool size between 15 and 20.

Active Screening for Malaria

For the cohort of the 505 asymptomatic individuals, using whole blood samples, microscopy failed to detect any infections, while RDT detected three. LE-PCR detected four positive samples, distinct from those detected by RDT, using pooled DBSs (Table 1). All 7 positive DBS samples were from children. The 7 corresponding whole blood samples were also tested by standard real-time qPCR, giving the same results as the ligation-enabled PCR. Follow-up visits 3 months later and reviews of medical history also indicated that the ligation-enabled PCR diagnoses were more reliable than those provided by RDT: none of the RDT-positive children showed malaria-related symptoms after the sampling day, although one of them had malaria-related symptoms 1 month before, and one of the ligation-enabled PCR-positive children developed malaria-related symptoms 10 days after sampling and was confirmed to have plasmodium vivax infection by local CDC. The remaining 3 ligation-enabled PCR-positive children developed malaria-related symptoms within 2 months after the sampling day. Due to the extremely limited local medical resources, they turned to private health care facilities for treatment without having any malaria tests performed.

TABLE 1

| Sample NO. | Active screening by LE-PCR | Standard real time qPCR | RNA hybridization assay (net RLU) | Clinical Symptom | RDT | Microscopy |
|---|---|---|---|---|---|---|
| 9 | — | — | — | — | RDT+ | — |
| 61 | — | — | — | — | RDT+ | — |
| 67 | — | — | — | — | RDT+ | — |
| 69 | 31.015 | 31.05 | 2.34E+06 | 1~2 moth | — | — |
| 80 | 33.87 | 34.115 | 2.31E+05 | Day 10 | — | — |
| 117 | 35.065 | 35.04 | 4.48E+05 | <1 month | — | — |
| 208 | 34.075 | 34.49 | 4.33E+05 | Within 2 week | — | — |

For the $2^{nd}$ cohort of subjects, we detected 10 infections from the 2855 DBSs, 8 of which were returned travelers while 2 were local residents. These results were consistent with microscopy on the whole blood samples. The 10 positive samples were also tested by real-time qPCR: 7 were proved to be *Plasmodium vivax* infections, 2 were *Plasmodium falciparum* infections and 1 was a mixed infection.

Discussion

In efforts to eliminate malaria, the objective of a malaria surveillance system is to stop local transmission by detecting and curing all malaria infections sufficiently early, whether symptomatic or not, including both locally transmitted and imported infections (Cotter et al., Lancet 382(9895): 900-11, 2013; W.H.O., World Malaria Report 2013). This necessitates active malaria screening for the entire at-risk population instead of the traditional passive diagnosis at clinics. It was recently proposed by the W.H.O. that in the elimination phase, all laboratory diagnostic services should be free of charge to patients (W.H.O., Disease Surveillance for malaria elimination: An operational manual, 2012). The need has never been greater for diagnostic methods capable of detecting extremely low levels of infection at low cost and in a high throughput fashion.

The *Plasmodium* 18S rRNA hybridization assay we described in our previous work showed better sensitivity and throughput than RDT and standard real time qPCR (Cheng et al., J. Clin. Microbiol. 51(1): 125-30, 2013), providing an ideal alternative for large scale screening of malaria in developed countries. However, for resource-limited areas where most malaria elimination efforts concentrate, the cost of the hybridization assay may present a problem. The ligation-enabled real-time qPCR method described in this study has a cost reduced by almost 90% compared to the previous RNA hybridization assay by significantly reducing the number of polynucleotide probes required and by substituting the expensive branched DNA detection system with common SYBR green-based real-time qPCR, while preserving the detection sensitivity and high sample throughput and maintaining a similar sample processing workflow. It is able to detect 18S rRNA of *Plasmodium falciparum* in a 96-well plate format, with a detection threshold as low as 0.01 p/µl in whole blood, and requiring no RNA purification or reverse transcription. The total cost is less than 2 dollars per test (including duplicate), while other RNA/DNA-based diagnostic methods may cost more for the RNA/DNA preparation procedures alone.

Implementation of a matrix pooling strategy as described in the present study allows for a further reduction in cost, while improving sample throughput. Unlike earlier tests of malaria employing pooling strategies (Taylor et al., J. Clin. Microbiol. 48(2): 512-9, 2010; Hsiang et al., J. Clinc Microbiol. 48(10): 3539-43, 2010), LE-PCR appears not to sacrifice any sensitivity when combined with pooling of DBSs; Ct values remained almost constant with increasing numbers of negative samples pooled with a single low-parasitemic sample for pool sizes of up to 36. This is not surprising as pooling of negative samples does not reduce the concentration of positive ones in the lysis mixture, and LE-PCR preferentially retains targeted RNA during the overnight hybridization. Off-target nucleic acids are washed off prior to formation of the PCR template. In this way, negative samples in each pool have little influence over the detection of positive ones.

In this study, for the active screening of asymptomatic individuals, LE-PCR cost less than 152 dollars (including duplicates) to detect all 4 infections out of 505 samples. Larger scale screening in low-transmission areas would yield an even lower cost per sample ratio, as the pool size could be increased, spreading the cost of each test across more samples. This is demonstrated in the active screening of the $2^{nd}$ cohort, where our strategy detected 10 infections out of 2855 DBSs using less than 400 tests, saving about 86% cost and labor compared to testing each sample individually.

PCR-based tests are well-known for requiring a high level of expertise, as well as for cross/carry-over contamination that is difficult to avoid. LE-PCR, on the other hand, suffers none of these problems. We had two clinical practitioners with little experience in molecular diagnostics trained for 5 days, and they were able to independently carry out LE-PCR using a matrix pooling strategy. Contamination is also easily avoidable in LE-PCR, since both the target nucleic acid and PCR template are anchored to the bottom of the plate until the real time qPCR process starts, and the plate is discarded without opening after real time qPCR is completed. In this way, both cross contamination and carry-over contamination are avoided.

LE-PCR, as is implemented in this study, becomes extraordinarily time efficient when screening large number of samples using a matrix pooling strategy. As samples are tested in parallel using 96-well plates with ELISA-like workflow, thousands of them could be diagnosed by a single technician in each run. In addition, LE-PCR is amenable to automation, which could further increase sample-processing capacity.

Subpatent infections in low-endemic settings may be the source of 20-50% of all transmission episodes (Okell et al., Nat. Commun. 3: 1237, 2012). In this study, LE-PCR successfully detected asymptomatic infections in 4 children that failed to be detected by both microscopy and RDT, with one of these children showing symptoms within 10 days after sampling. Should LE-PCR-based active screening become a daily routine, its 3-day turnaround time would be sufficient to aid in getting treatment to asymptomatic patients like this child, allowing them to avoid suffering from the disease and helping to remove a significant source of infection of others.

Overprescribing of antimalarials to people without malaria infection is still prevalent, leading to unnecessary side-effects and increased risk of drug-resistance (W.H.O., World Malaria Report: 2014; Sansom, Lancet Infec. Dis. 9(10): 596, 2009; W.H.O., WHO informal consultation on fever management in peripheral health care settings: A global review of evidence and practice, 2013). Recommended by the W.H.O. (W.H.O., WHO informal consultation on fever management in peripheral health care settings: A global review of evidence and practice, 2013), RDT has been successfully implemented to exclude many parasite-negative patients from receiving antimalarials (W.H.O., World Malaria Report: 2014). However, as is shown in this study, RDT may not be enough to stop overprescription of antimalarials: for the 3 RDT-positive children in this study, they were determined to be parasite-negative by standard real-time qPCR (Rougemont et al., J. Clin. Microbiol. 42(12): 5636-43, 2004), RNA hybridization assay (Cheng et al., J. Clin. Microbiol. 51(1): 125-30, 2013), and LE-PCR, indicating that RDT diagnostics may be insufficient to eliminate overprescription. LE-PCR, on the other hand, showed a 0% false-positive rate, as determined by comparison with diagnosis using standard real time qPCR, and if implemented as a routine active screening diagnostic for malaria detection could significantly reduce the likelihood of overprescription.

As a part of worldwide malaria eradication efforts, identification of locally transmitted or imported malaria infections in resource-limited, at-risk districts can now be carried out using a strategy as follows: First, dried blood spots are collected by local disease-control agencies in active screenings and sent to a central clinical laboratory by mail; the lab then tests the samples batch-wise in a 96-well plate format using ligation-enabled real time qPCR with a pooling strategy (one technician in a single run can easily process hundreds of tests on pooled samples from thousands of individuals); positive samples are identified within 2 to 3 days, and an additional day may be included for confirmation and species identification using standard qPCR; the results are quickly fed back to the local and state monitoring agencies via networked rapid communications. The total turnaround time should be within a week, allowing time for implementation of effective interventional strategies, thus minimizing the transmission of the disease.

Example 2: Specific Detection of Non-Coding RNA

Figure 7:
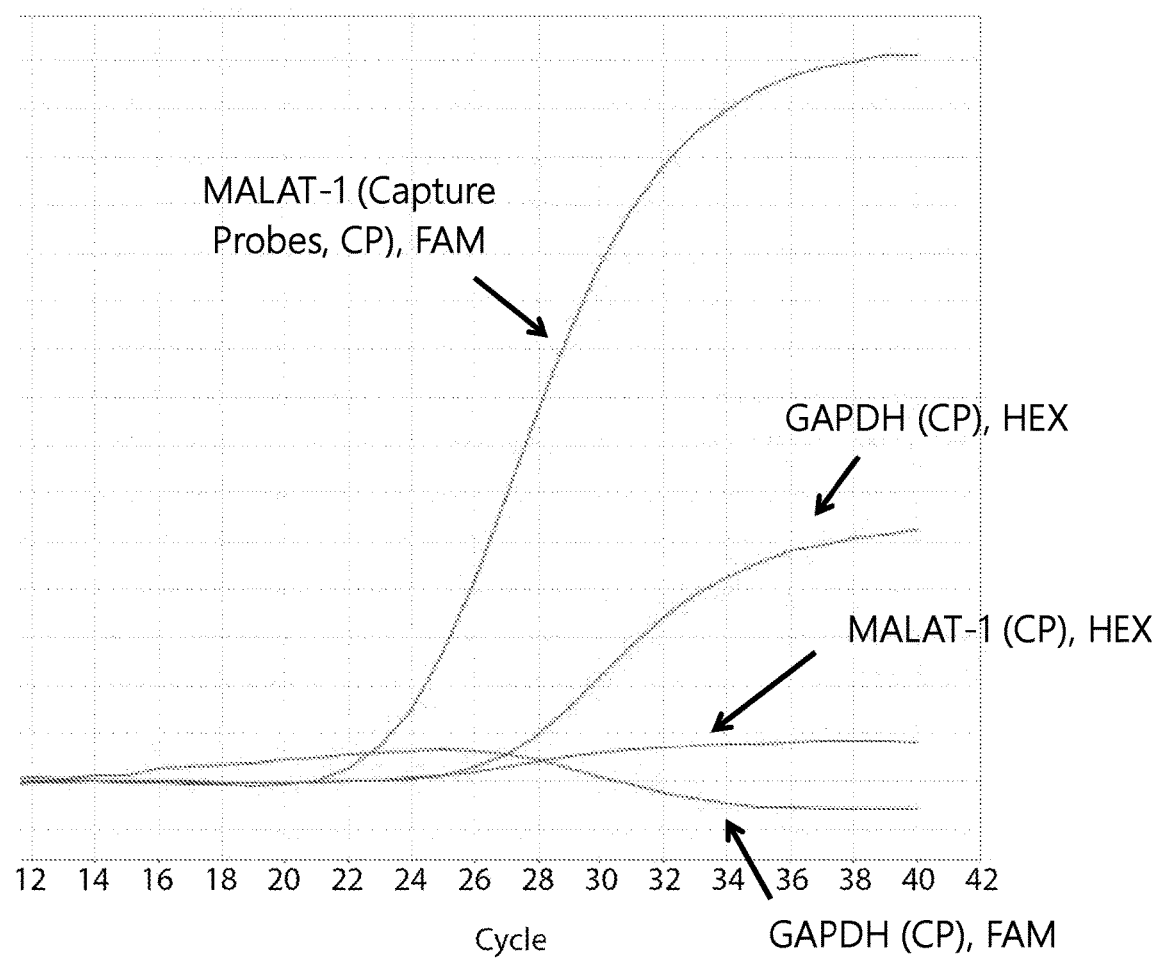
FIG. 7 shows the specific detection of non-coding RNA by LE-PCR combined with RT-qPCR using Taqman probes.

To monitor the level of the long non-coding RNA MALAT in cultured cells, we first made a 10-fold serial dilution of lysed cells, and then tested the lysates using LE-PCR. Using a range of 34 cells/well to 34400 cells/well, the assay showed a good correlation between Ct and cell number ($R^2$=0.96, FIG. 1), demonstrating the quantitative nature of the assay. To determine the specificity of the assay, real-time qPCR was performed with taqman probes specific for either MALAT (FAM-labeled) or GAPDH (HEX-labeled) using LE-PCR probes for either MALAT or GAPDH. Amplification was detected only when MALAT capture extenders were used with MALAT taqman probes, or when GAPDH capture extenders were used with GAPDH taqman probes (FIG. 7). This result shows the assay is highly specific. Multiplex detection of MALAT/GAPDH using mixed sets of probes was also performed (data not shown).

Example 3: Detection of Influenza A/B and Parainfluenza Virus 1

Figure 8A:
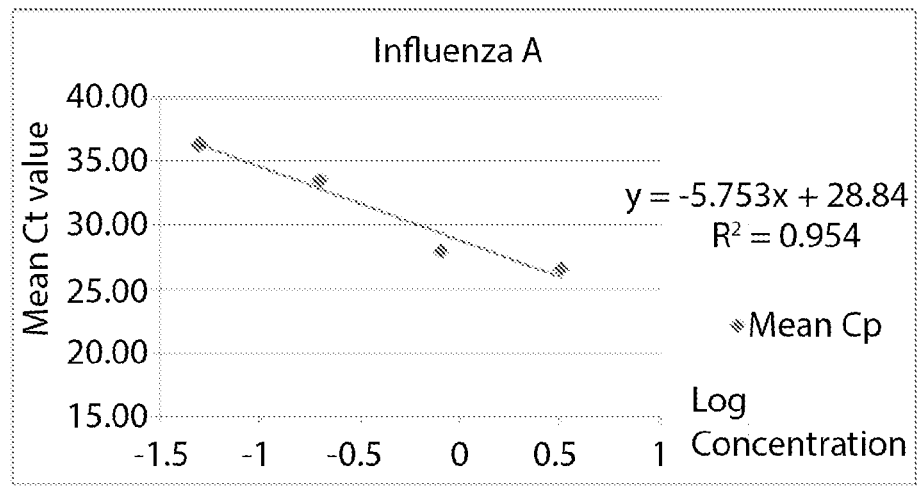
FIGS. 8A, 8B and 8C show the sensitivity of LE-PCR for detecting influenza A/B and parainfluenza virus 1 IVT-RNA.
Figure 8B:
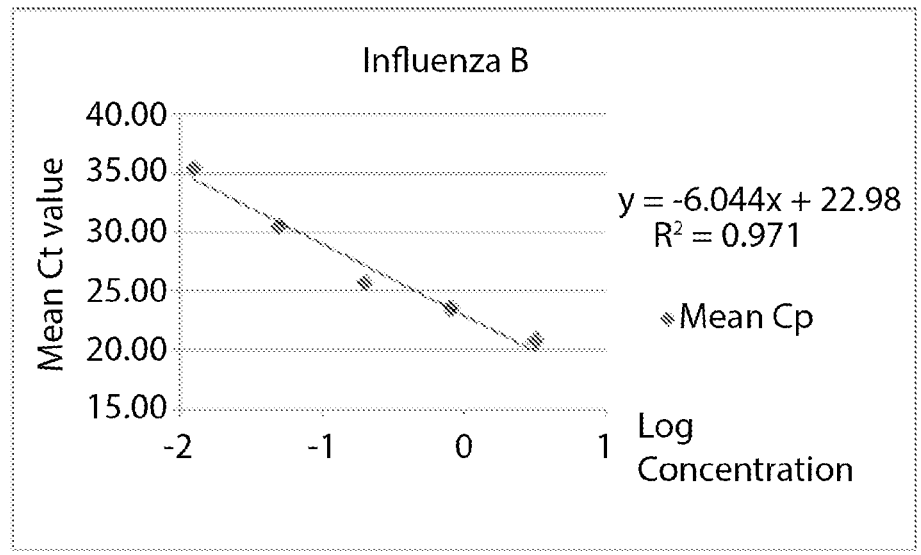
Figure 8C:
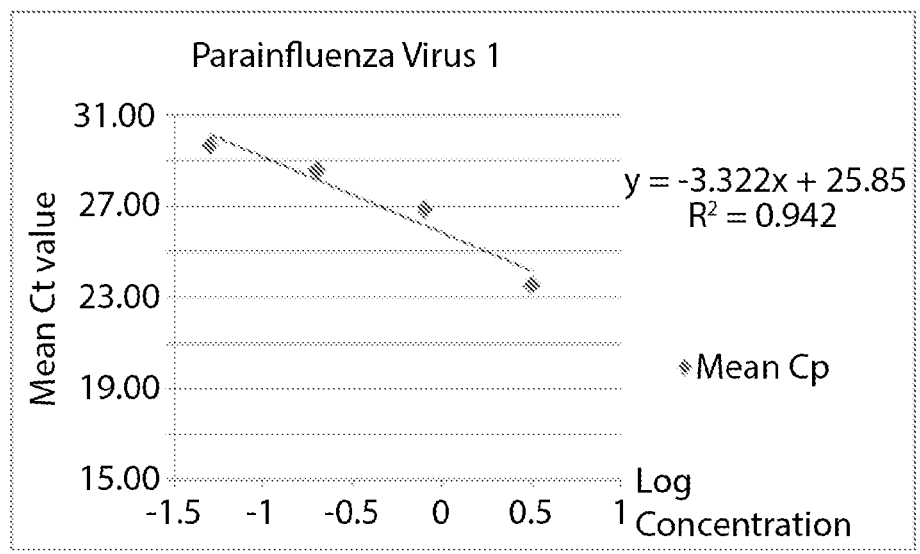

The threshold of LE-PCR for detecting the presence of influenza A/B and parainfluenza was assayed as previously described in Example 1 for *Plasmodium falciparum*, using serial dilutions of in vitro-transcribed RNA corresponding to each virus, and was found to be as low as 7528 IVT-RNA molecules per 100 ul reaction (FIGS. 8A, 8B and 8C).

Example 4: Detection from Nasal and Pharyngeal Swab

We also tested LE-PCR with clinical nasal and pharyngeal swab samples. Nasal and pharyngeal swab specimens were collected from influenza patients (n=13). The samples were diagnosed using LE-PCR as described in Example 1, as well as by Seeplex™ RV kit (Seegene, Korea). Our LE-PCR assay had 80% concordance with the results of Seeplex™ RV kit for influenza B and 75% concordance with the results for influenza A.

Example 5: Workflow of LE-PCR

Figure 9:
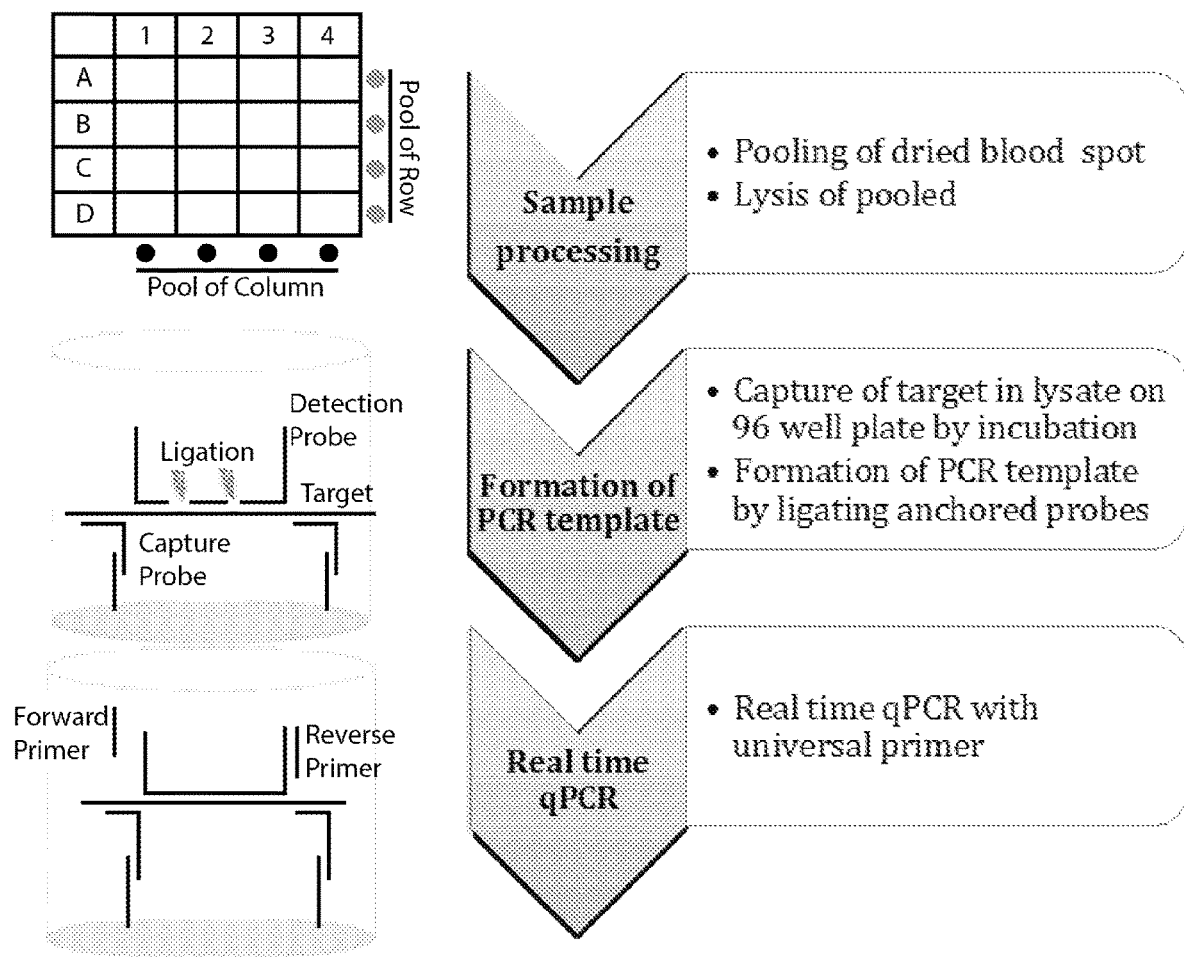
FIG. 9 shows a schematic of the workflow of LE-PCR.

LE-PCR includes three steps. First, sample processing: dried blood samples are lysed in one step to release 18S rRNA. Second, formation of PCR template: during overnight incubation with sample lysate, capture extenders and detection probes hybridize to contiguous sequences in a highly conserved region of *Plasmodium* 18S ribosomal RNA; tails of capture extenders hybridize to capture probes pre-conjugated to the surface of wells in a 96-well plate, while tails of detection probes provide universal primer binding sites; the unbound probes are washed off while detection probes, which hybridize adjacent to each other, are ligated to form a single ssDNA that contains the universal primer binding sites. Third, real time qPCR: the ssDNA formed in the previous step is used as PCR template with the universal primers. See FIG. 9.

SEQUENCES

Detection probe 1
TGGAAGTATTTTAGACAAATGCTTTCTTTTTGGTCATAGCTGTTTCCTG
(SEQ ID NO: 1)

Detection probe 2
TGTAAAACGACGGCCAGTTTTTTCGACGGTATCTGATCGTCTTCACT
(SEQ ID NO: 2)

Internal detection probe
CCCTTAACTTTCGTTCTTGATTAA (SEQ ID NO: 3)

Capturing sequence 1
TCTAAGAATTTCACCTCTGACATCTG (SEQ ID NO: 4)

Capturing sequence 2
GCAGTTGTTCGTCTCCAGAAAA (SEQ ID NO: 5)

Capturing sequence 3
TCGGCATAGTTTATGGTTAAGATTA (SEQ ID NO: 6)

PCR primer 1
TGTAAAACGACGGCCAGT (SEQ ID NO: 7)

PCR primer 2
CAGGAAACAGCTATGACC (SEQ ID NO: 8)

The invention claimed is:

1. A method of detecting a target nucleic acid in a biological sample, comprising:
   a) capturing the target nucleic acid through a plurality of capture extenders, wherein each of the capture extenders comprises a capturing sequence that hybridizes to a region on the same target nucleic acid and an immobilizing sequence that hybridizes to a capture probe conjugated to a solid support, thereby immobilizing the target nucleic acid to the solid support;
   b) contacting the target nucleic acid with a plurality of detection probes, wherein each of the plurality of detection probes comprises a sequence that hybridizes to a region on the same strand of the same target nucleic acid;
   c) ligating the plurality of detection probes hybridized to the target nucleic acid to form a ligated detection sequence;
   d) amplifying the ligated detection sequence; and
   e) detecting the amplified ligated detection sequence.

2. The method of claim 1, wherein the plurality of detection probes comprises a 5' detection probe and a 3' detection probe, wherein the 5' detection probe is phosphorylated at its 5' end.

3. The method of claim 2, wherein the plurality of detection probes further comprises at least one internal detection probe that hybridizes to a region between the region where the 5' probe hybridizes and the region where the 3' probe hybridizes, wherein the internal detection probe is phosphorylated at its 5' end.

4. The method of claim 1, wherein the ligating step is carried out by a ligase enzyme.

5. The method of claim 1, wherein steps a) and b) are carried out concurrently.

6. The method of claim 1, further comprising filling in any gaps between detection probes hybridized to the target nucleic acid by treatment with a DNA polymerase or reverse transcriptase.

7. The method of claim 1, wherein the amplifying step comprises PCR amplification using a first primer complementary to a region on the 5' detection probe and a second primer corresponding in sequence to a region on the 3' detection probe.

8. The method of claim 1, wherein the target nucleic acid is RNA.

9. The method of claim 8, wherein the RNA is mRNA, ribosomal RNA, a splice isoform of an mRNA, non-coding RNA, or circulating RNA.

10. The method of claim 1, wherein the target nucleic acid is DNA.

11. The method of claim 1, wherein the biological sample is a cell lysate.

12. The method of claim 1, wherein the biological sample is selected from the group consisting of a cell lysate, a tissue homogenate, a blood sample, a dried blood spot, a plasma sample, a serum sample, a blood clot, a nasal swab, a pharyngeal swab, a cheek swab, urine, and saliva.

13. The method of claim 1, wherein the method is high throughput.

14. The method of claim 1, further comprising diagnosing a disease in an individual, wherein the disease is caused by a pathogen comprising the target nucleic acid, wherein detection of the target nucleic acid indicates a positive diagnosis of the disease in the individual.

15. The method of claim 1, further comprising detecting a genetic variation associated with a disease, wherein the target nucleic acid comprises the variation and at least one of the plurality of detection probes can hybridize to a region of the target nucleic acid comprising all or a portion of the variation.

16. The method of claim 1, wherein the target nucleic acid is an exogenous nucleic acid.

17. A method of detecting a plurality of target nucleic acids in a biological sample, comprising:
   a) capturing one of the plurality of target nucleic acids through a plurality of capture extenders, wherein each of the capture extenders comprises a capturing sequence that hybridizes to a region on one of the target nucleic acids and an immobilizing sequence that hybridizes to a capture probe conjugated to a solid support, thereby immobilizing the target nucleic acid to the solid support;
   b) contacting the same one of the plurality of target nucleic acids with a plurality of detection probes comprising a first primer binding site and a second primer binding site, wherein each of the plurality of detection probes comprises a sequence that hybridizes to a region on the target nucleic acid;
   c) carrying out steps a) and b) for each of the plurality of target nucleic acids;
   d) ligating the plurality of detection probes to form a plurality of ligated detection sequences specific to each of the plurality of target nucleic acids;
   e) amplifying the plurality of ligated detection sequences; and f) detecting the plurality of amplified ligated detection sequences.

18. The method of claim 17, wherein the first primer binding site is a first generic primer binding site common to of each of the plurality of detection probes, the second primer binding site is a second generic primer binding site common to each of the plurality of detection probes, and the amplification step is carried out using a pair of generic PCR primers corresponding to the first and second generic primer binding sites.

* * * * *